(12) United States Patent
Kiani

(10) Patent No.: US 12,428,685 B2
(45) Date of Patent: Sep. 30, 2025

(54) VIRAL DETECTION USING TEMPLATE EMULSIFICATION

(71) Applicant: ILLUMINA, INC., San Diego, CA (US)

(72) Inventor: Sepehr Kiani, Watertown, MA (US)

(73) Assignee: Illumina, Inc., San Diego, CA (US)

( * ) Notice: Subject to any disclaimer, the term of this patent is extended or adjusted under 35 U.S.C. 154(b) by 253 days.

(21) Appl. No.: 17/210,737

(22) Filed: Mar. 24, 2021

(65) Prior Publication Data

US 2021/0301354 A1    Sep. 30, 2021

Related U.S. Application Data

(60) Provisional application No. 62/993,954, filed on Mar. 24, 2020.

(51) Int. Cl.
*C12Q 1/6888* (2018.01)
*C12Q 1/6869* (2018.01)
*C12Q 1/70* (2006.01)

(52) U.S. Cl.
CPC ......... *C12Q 1/6888* (2013.01); *C12Q 1/6869* (2013.01); *C12Q 1/701* (2013.01)

(58) Field of Classification Search
CPC ...... C12Q 1/6888; C12Q 1/686; C12Q 1/701; C12Q 1/70; C12Q 2563/159; C12Q 2563/179; C12Q 1/6869; C12N 15/1006; G01N 33/569; G01N 33/56983
See application file for complete search history.

(56) References Cited

U.S. PATENT DOCUMENTS

| | | | |
|---|---|---|---|
| 4,701,415 A | 10/1987 | Dutton |
| 5,512,439 A | 4/1996 | Hornes et al. |
| 5,813,759 A | 9/1998 | Gebrian |
| 6,210,891 B1 | 4/2001 | Nyren et al. |
| 6,306,597 B1 | 10/2001 | Macevicz |
| 6,309,833 B1 | 10/2001 | Edman et al. |
| 6,828,100 B1 | 12/2004 | Ronaghi |
| 6,833,246 B2 | 12/2004 | Balasubramanian |
| 6,911,345 B2 | 6/2005 | Quake et al. |
| 7,232,656 B2 | 6/2007 | Balasubramanian et al. |
| 7,537,897 B2 | 5/2009 | Brenner et al. |
| 7,598,035 B2 | 10/2009 | Macevicz |
| 7,835,871 B2 | 11/2010 | Kain et al. |
| 7,842,457 B2 | 11/2010 | Berka et al. |
| 7,960,120 B2 | 6/2011 | Rigatti et al. |
| 8,012,690 B2 | 9/2011 | Berka et al. |

(Continued)

FOREIGN PATENT DOCUMENTS

| AU | 2013203624 A1 | 5/2013 |
|---|---|---|
| EP | 3819637 A1 | 5/2021 |

(Continued)

OTHER PUBLICATIONS

Bowman, 2013, Multiplexed Illumina sequencing libraries from picogram quantities of DNA, BMC Genomics 14:466 (8 pages).

(Continued)

*Primary Examiner* — Sarae L Bausch
(74) *Attorney, Agent, or Firm* — Illumina, Inc.

(57) ABSTRACT

The disclosure provides methods and systems for multiplex viral detection using monodisperse emulsion droplets and template particles.

24 Claims, 9 Drawing Sheets

(56) References Cited

U.S. PATENT DOCUMENTS

| | | |
|---|---|---|
| 8,629,323 B2 | 1/2014 | Weeks |
| 8,715,934 B2 | 5/2014 | Diehl et al. |
| 8,748,102 B2 | 6/2014 | Berka et al. |
| 8,765,380 B2 | 7/2014 | Berka et al. |
| 9,011,777 B2 | 4/2015 | Beer |
| 9,012,390 B2 | 4/2015 | Holtze et al. |
| 9,085,798 B2 | 7/2015 | Chee |
| 9,260,751 B2 | 2/2016 | Diehl et al. |
| 9,388,465 B2 | 7/2016 | Hindson et al. |
| 9,399,797 B2 | 7/2016 | Hutchison et al. |
| 9,562,837 B2 | 2/2017 | Link |
| 9,567,645 B2 | 2/2017 | Fan et al. |
| 9,567,646 B2 | 2/2017 | Fan et al. |
| 9,580,736 B2 | 2/2017 | Tan et al. |
| 9,598,736 B2 | 3/2017 | Fan et al. |
| 9,637,799 B2 | 5/2017 | Fan et al. |
| 9,650,629 B2 | 5/2017 | Froehlich et al. |
| 9,695,474 B2 | 7/2017 | Johnson et al. |
| 9,701,998 B2 | 7/2017 | Hindson et al. |
| 9,708,654 B2 | 7/2017 | Hunicke-Smith et al. |
| 9,783,847 B2 | 10/2017 | Chee |
| 9,951,386 B2 | 4/2018 | Hindson et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,151,003 B2 | 12/2018 | Fan et al. |
| 10,155,981 B2 | 12/2018 | Brenner et al. |
| 10,202,628 B2 | 2/2019 | Church et al. |
| 10,208,356 B1 | 2/2019 | Fan et al. |
| 10,221,442 B2 | 3/2019 | Hindson et al. |
| 10,240,192 B2 | 3/2019 | Berka et al. |
| 10,240,197 B1 | 3/2019 | Brenner et al. |
| 10,253,375 B1 | 4/2019 | Fan et al. |
| 10,266,883 B2 | 4/2019 | Chee |
| 10,280,459 B1 | 5/2019 | Brenner et al. |
| 10,285,940 B2 | 5/2019 | Mason et al. |
| 10,329,557 B2 | 6/2019 | Johnson et al. |
| 10,344,329 B2 | 7/2019 | Hindson et al. |
| 10,392,662 B1 | 8/2019 | Brenner et al. |
| 10,400,280 B2 | 9/2019 | Hindson et al. |
| 10,415,030 B2 | 9/2019 | Marshall et al. |
| 10,457,986 B2 | 10/2019 | Hindson et al. |
| 10,501,793 B2 | 12/2019 | Chee |
| 10,584,381 B2 | 3/2020 | Hindson et al. |
| 11,001,901 B1 * | 5/2021 | Donati ............... C12N 15/1096 |
| 11,060,149 B2 | 7/2021 | Steelman |
| 11,104,961 B2 | 8/2021 | Fontanez et al. |
| 11,142,791 B2 | 10/2021 | Abate et al. |
| 2002/0132251 A1 | 9/2002 | Shuber |
| 2003/0143599 A1 | 7/2003 | Makarov et al. |
| 2003/0180737 A1 | 9/2003 | Gu et al. |
| 2004/0005585 A1 | 1/2004 | Bi et al. |
| 2006/0024681 A1 | 2/2006 | Smith et al. |
| 2006/0177836 A1 | 8/2006 | McKernan et al. |
| 2006/0292611 A1 | 12/2006 | Berka et al. |
| 2007/0080316 A1 | 4/2007 | Sauer et al. |
| 2007/0114362 A1 | 5/2007 | Feng et al. |
| 2008/0004436 A1 | 1/2008 | Tawfik |
| 2009/0280475 A1 | 11/2009 | Pollack et al. |
| 2011/0009278 A1 | 1/2011 | Kain et al. |
| 2011/0086780 A1 | 4/2011 | Colston, Jr. et al. |
| 2011/0118151 A1 | 5/2011 | Eshoo et al. |
| 2011/0311978 A1 | 12/2011 | Makarewicz, Jr. et al. |
| 2012/0295269 A1 | 11/2012 | Pourahmadi et al. |
| 2012/0316074 A1 | 12/2012 | Saxonov |
| 2013/0115169 A1 | 5/2013 | Lahann et al. |
| 2014/0155295 A1 | 6/2014 | Hindson et al. |
| 2015/0133312 A1 | 5/2015 | Bielas et al. |
| 2015/0225777 A1 | 8/2015 | Hindson et al. |
| 2016/0186267 A1 | 6/2016 | So et al. |
| 2016/0250608 A1 | 9/2016 | Anders et al. |
| 2016/0274103 A1 | 9/2016 | Piloto et al. |
| 2017/0192030 A1 | 7/2017 | Lapham et al. |
| 2017/0218437 A1 | 8/2017 | Seul et al. |
| 2017/0232417 A1 | 8/2017 | Lebofsky et al. |
| 2017/0255160 A1 | 9/2017 | Numata et al. |
| 2018/0010105 A1 | 1/2018 | Rogers et al. |
| 2018/0051321 A1 | 2/2018 | Hindson et al. |
| 2018/0119216 A1 | 5/2018 | Jamshidi et al. |
| 2018/0133715 A1 | 5/2018 | Craig et al. |
| 2018/0179553 A1 | 6/2018 | Watson et al. |
| 2018/0216162 A1 | 8/2018 | Belhocine et al. |
| 2018/0237836 A1 | 8/2018 | Abate et al. |
| 2018/0274027 A1 | 9/2018 | Hindson et al. |
| 2018/0355407 A1 | 12/2018 | Utharala et al. |
| 2019/0085412 A1 | 3/2019 | Fan et al. |
| 2019/0153532 A1 | 5/2019 | Bharadwaj et al. |
| 2019/0153550 A1 | 5/2019 | Steinmetzer et al. |
| 2019/0177789 A1 | 6/2019 | Hindson et al. |
| 2019/0323003 A1 | 10/2019 | Ramji et al. |
| 2019/0323091 A1 | 10/2019 | Bramlett et al. |
| 2019/0352714 A1 | 11/2019 | Salk et al. |
| 2019/0381497 A1 | 12/2019 | Di Carlo et al. |
| 2019/0382753 A1 | 12/2019 | Steemers et al. |
| 2020/0040385 A1 | 2/2020 | Beechem et al. |
| 2020/0080112 A1 | 3/2020 | Zhang et al. |
| 2020/0190513 A1 | 6/2020 | Fernandez et al. |
| 2020/0261879 A1 | 8/2020 | Abate et al. |
| 2020/0324287 A1 | 10/2020 | Vijayan et al. |
| 2020/0376488 A1 | 12/2020 | Wu et al. |
| 2021/0010070 A1 | 1/2021 | Schnall-Levin et al. |
| 2021/0054369 A1 | 2/2021 | Meltzer et al. |
| 2021/0214721 A1 | 7/2021 | Fontanez et al. |
| 2021/0214763 A1 | 7/2021 | Fontanez et al. |
| 2021/0214769 A1 | 7/2021 | Fontanez et al. |
| 2021/0214792 A1 | 7/2021 | Fontanez et al. |
| 2021/0214802 A1 | 7/2021 | Fontanez et al. |
| 2021/0215591 A1 | 7/2021 | Fontanez et al. |
| 2021/0301354 A1 | 9/2021 | Kiani |
| 2021/0332432 A1 | 10/2021 | Kiani |
| 2021/0340596 A1 | 11/2021 | Meltzer et al. |
| 2021/0381064 A1 | 12/2021 | Fontanez et al. |
| 2022/0017892 A1 | 1/2022 | Meltzer et al. |
| 2022/0135966 A1 | 5/2022 | Meltzer |
| 2022/0136071 A1 | 5/2022 | Meltzer |
| 2022/0154248 A1 | 5/2022 | Abate et al. |
| 2022/0235416 A1 | 7/2022 | Fontanez et al. |
| 2022/0267761 A1 | 8/2022 | Fontanez et al. |

FOREIGN PATENT DOCUMENTS

| | | |
|---|---|---|
| JP | 2021072863 A | 5/2021 |
| WO | 1997/008547 A1 | 3/1997 |
| WO | 2010/117620 A2 | 10/2010 |
| WO | 2011/047307 A1 | 4/2011 |
| WO | 2012/116146 A1 | 8/2012 |
| WO | 2012/149042 A2 | 11/2012 |
| WO | 2013/165748 A1 | 11/2013 |
| WO | 2014/028537 A1 | 2/2014 |
| WO | 2014/100434 A1 | 6/2014 |
| WO | 2014/146025 A1 | 9/2014 |
| WO | 2014/153071 A1 | 9/2014 |
| WO | 2015/157369 A1 | 10/2015 |
| WO | 2015/187792 A1 | 12/2015 |
| WO | 2016/025815 A1 | 2/2016 |
| WO | 2016/040476 A1 | 3/2016 |
| WO | 2016/126871 A2 | 8/2016 |
| WO | 2016/138080 A1 | 9/2016 |
| WO | 2016/172373 A1 | 10/2016 |
| WO | 2017/161306 A1 | 9/2017 |
| WO | 2019/011971 A1 | 1/2019 |
| WO | 2019/023627 A1 | 1/2019 |
| WO | 2019/139650 A2 | 7/2019 |
| WO | 2019/157529 A1 | 8/2019 |
| WO | 2019/204229 A1 | 10/2019 |
| WO | 2019/217552 A1 | 11/2019 |
| WO | 2019/222523 A2 | 11/2019 |
| WO | 20200037214 A1 | 2/2020 |

(56) References Cited

FOREIGN PATENT DOCUMENTS

| WO | 2020/069268 A1 | 4/2020 |
| WO | 2020/069298 A1 | 4/2020 |

OTHER PUBLICATIONS

Eastbum, 2013, Ultrahigh-trhoughput mammalian single-cell reverse-transcriptase polymerase chain reaction in microfluidic drops, Anal Chem 85:8016-8021.
Figueiredo, 2007, Cost effective method for construction of high quality cDNA libraries, Biomol Eng 24:419-421.
Fu, 2015, Uniform and accurate single-cell sequencing based on emulsion whole-genome amplification, PNAS 112 (38):11923-11928.
Hatori, 2019, Particle-Templated Emulsification for Microfluidics-Free Digital Biology, Analytical Chemistry, 90:9813-9820.
Int Search Report and Written Op mailed Apr. 1, 2021, for Int Application No. PCT/US2021/013069, filed Jan. 12, 2021 (14 pages).
Int Search Report and Written Op mailed Aug. 11, 2021, for Int Application No. PCT/US2021/022503, filed Mar. 16, 2021 (9 pages).
Int Search Report and Written Op mailed Feb. 2, 2021, for Int Application No. PCT/US2020/47214, filed Aug. 20, 2020 (14 pages).
Int Search Report and Written Op mailed Jun. 30, 2021, for Int Application No. PCT/US2021/023815, filed Mar. 24, 2021 (14 pages).
Int Search Report and Written Op mailed Mar. 29, 2021, for Int Application No. PCT/US2021/013042, filed Jan. 12, 2021 (9 pages).
Int Search Report and Written Op mailed Mar. 29, 2021, for Int Application No. PCT/US2021/013045, filed Jan. 12, 2021 (8 pages).
Int Search Report and Written Op mailed Mar. 29, 2021, for Int Application No. PCT/US2021/013065, filed Jan. 12, 2021 (11 pages).
Int Search Report and Written Op mailed Mar. 29, 2021, for Int Application No. PCT/US2021/013066, filed Jan. 12, 2021 (11 pages).
Int Search Report and Written Op mailed Mar. 31, 2021, for Int Application No. PCT/US2021/013048, filed Jan. 12, 2021 (20 pages).
Kumaresan, 2008, High-throughput single copy DNA amplification and cell analysis in engineered nanoliter droplets, Anal Chem, 80:3522-3529.
Kumari, 2017, Quantification of Circulating Free DNA as a Diagnostic Marker in Gall Bladder Cancer, Pathology & Oncology Research, 23:91-97.
Lage, 2003, Whole genome analysis of genetic alterations in small DNA samples using hyperbranched strand displacement amplification and array-CGH, Genome Res 13:294-307.
Lyons, 2017, Large-scale DNA barcode library generation for biomolecule identification in high-throughput screens, Sci Rep 7:13899 (7 pages).
Mazutis, 2013, Singl-cell analysis and sorting using droplet-based microfluidics, Nature Protocols, 8(5):870-891.
Nishikawa, 2015, Monodisperse picoliter droplets for low-bias and contamination-free reactions in single-cell whole genome amplification, PLoSOne 10(9):e0138733 (15 pages).
Roche, 2011, emPCR amplificaiotn method manual, 454 Life Sciences Corp (12 pages).
Sidore, 2016, Enhanced sequencing coverage with digital droplet multiple displacement amplification, Nucl Acids Res 44(7):e66 (9 pages).
Stoeckius, 2017, Simultaneous epitope and transcriptome measurment in single cells, Nat Meth online pub (10 pages).
Tamminen, 2015, Single gene-based distinction of individual microbial genomes from a mixed population of microbial cells Front Microb 6:195 (10 pages).
Vitale, 2019, An Optimized Workflow to Evaluate Estrogen Receptor Gene Mutations in Small Amounts of Cell-Fee DNA, The Journal of Molecular Diagnostics, 21(1):123-127.
Walls, 2020, Structure, Function, and Antigenicity of the SARS-CoV-2 Spike Glcoprotein, Cell, 181(2):281-292.
Zilionis, 2016, Single-cell barcoding and sequencing using droplet microfluidics, Natutre Prot 12(1):44-73.
Berensmeier, 2006, Magnetic particles for the separation and purification of necleic acids, Applied Microbiology and Biotechnology, 73:495-504.
Biocompare, 2013, How to maintain a constant temp in your CO2 incubator, 17 Janaury 2013 (Jan. 17, 2013) [online] retrieved from <URL: https://www.biocompare.com/Editorial-Articles/126328-Incubators/#:~text=A jacket of water circulates, thermal buffer against outside air.> entire document, 7 pages.
Brouzes, 2009, Droplet microfluidic technology for single-cell high-throughput screening, Proc Natl Acad Sci 106 (34):14195-14200.
Cai, 2019, Selection of DNA-encoded libraries to protein targets within and on living cells, Journal of the American Chemical Society, 141(43):1-11.
Cheng, 2020, Ultra-senstive and rapid detection of nucleic acids and microorganisms in body fluids using single molecule tethering, Nature Communications, 11(1):1-9.
Datlinger, 2017, Pooled CRISPR screening with single-cell transcriptome readout, Nature Methods 4(3):297-301.
High containment laboratories at CDC—Fifty Years of Excellence, Centers for Disease Control and Prevention, retreived from the internet, <https://www.cdc.gov/ncezid/dhcpp/hcl-50/high-containment-laboratories.html>, 1 page.
Jacobsen, 2004, Direct isolation of poly(A)+ RNA from 4 M guanidine thiocyanate-lysed cell extracts using locked nucleic acid-oligo(T) capture, Nucleic Acids Research, 32(7), 10 pages.
Kim, 2018, Single-Cell RT-PCR in Microfluidic Droplets with Integrated Chemical Lysis, Anal Chem 90(2): 1273-1279.
Klein, 2015, Droplet barcoding for single cell transcriptomics applied to embryonic stem cells, Cells, 161(5):1187-1201.
Kukurba, 2015, RNA Sequencing and Analysis, Cold Spring Harb Protoc 11:951-969.
Markus, 2021, Analysis of recurrently protected genomic regions in cell-free DNA found in urine, Science Translational Medicine, 13(581):1-31.
Patel, 2019, Design and fabrication of low cost vortex mixer using additive manufacturing, International Journal of Applied Engineering Research 14(1):246-249.
Petersen, 2021, Screening of DNA-encoded small molecule libraries inside a living cell, Journal of the American Chemical Society, 143(7):2751-2756.
Quail, 2012, A tale of three next generation sequencing platforms: comparison of Ion Torrent, Pacific Biosciences and Illumina MiSeq sequencers, BMC Genomics 13:341, 13 pages.
Replogle, 2020, Combinatorial single-cell CRISPR screens by direct guide RNA capture and targeted sequencing, Nat. Biotechnol. 38(8):954-961.
Stoeckius, 2017, Large-scale simultaneous measurements of epitopes and transcriptomes in single cells, Nat Methods 14(9):865-868.
Tokunaga, 2013, Systematic exploration of lipophilic tags that allow efficient anchoring of aptamers to live cell surfaces, Chem Lett 42(2):127-129.

* cited by examiner

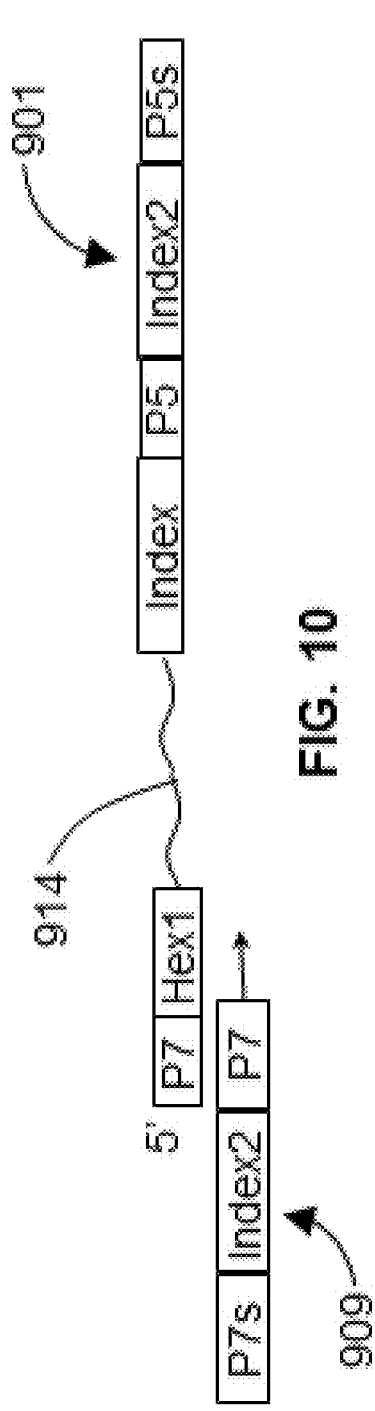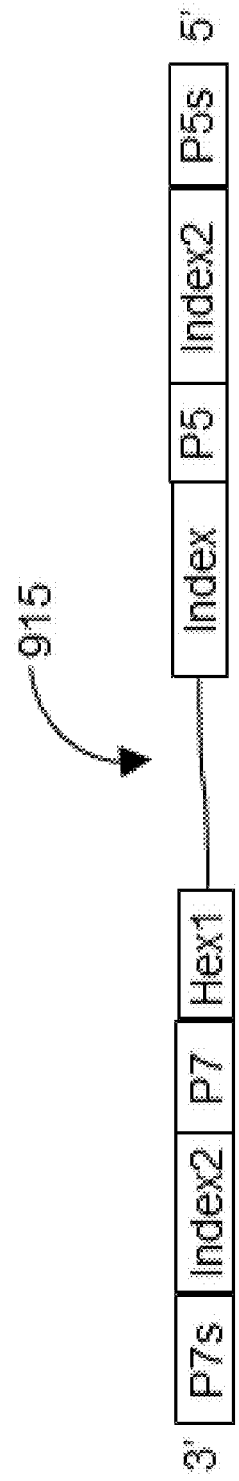

VIRAL DETECTION USING TEMPLATE EMULSIFICATION

CROSS REFERENCE

This application claims the benefit of U.S. Provisional Patent Application No. 62/993,954, filed on Mar. 24, 2020, the contents of which are incorporated herein by reference.

TECHNICAL FIELD

The disclosure relates to tools for determining the presence of viruses or sequencing viral genomes in biological systems.

BACKGROUND

Rapid and accurate diagnostic testing for viral infection is of paramount import. The need for such testing has been highlighted during the emergence and outbreak of several novel viruses. Viruses are emerging or re-emerging at an accelerated rate. (see, Côté and Feng, Viruses (2018)). Emerging viruses include extant human viruses that have undergone mutation and zoonotic viruses. Since the year 2000, notable zoonosis outbreaks include the avian flu, swine flu, Ebola, Zika, West Nile fever, SARS, MERS, and COVID-19. The spread of COVID-19, caused by SARS-COV-2, reveals the need for the rapid development and implementation of flexible diagnostic and epidemiological tools to monitor and prevent the spread of emerging viruses. This need is especially pronounced when, as with SARS-COV-2, patients infected with a particular virus are asymptomatic or present symptoms that overlap with other diseases.

There are several modalities for testing whether a patient is infected with a particular virus. Many contemporary testing modalities are hampered by severe drawbacks, including high cost, the need for specialized facilities and personnel, extended turn-around-time (TAT), limited reference databases, and the need to research and develop virus-specific reagents. (see, Souf, Biohorizons, vol. 9 (2016), incorporated by reference).

PCR-based assays have become the standard testing modality for many viruses. These assays can be simple and effective. Quantitative-PCR and reverse transcription-PCR (RT-PCR) assays have the added ability of assessing viral load. However, current PCR-based testing methods have their own drawbacks. Many PCR-based testing methods require specialized microfluidics or testing chips along with the trained personnel to use them. Without trained personnel, PCR-based viral testing is prone to errors, especially false-positive results. Additionally, PCR-based methods often require a time-consuming process to develop and validate specific primers. Depending on the test, primers may need to be specific not only for a particular viral species, but specific for a viral subtype, strain, or substrain. Stringent primer specificity is often required because many viruses, particularly retro- and RNA viruses, are prone to frequent mutation. Thus, accurate discrimination between an emerging virus and a wide panel of alternative infectious agents is complicated by the need to develop compatible and specific primer sets for multiplex PCR panels. As a result, testing a patient for a panel of diseases often requires running multiple individual tests in parallel.

The spread of SARS-COV-2 elucidated the drawbacks of current viral testing modalities. Months after the novel virus was identified, there was still a lack of rapid and accurate testing. Additionally, there was no test that could discriminate SARS-COV-2 from seasonal influenza, which presents many overlapping symptoms. Inadequate testing prevented infected individuals from being quickly diagnosed and isolated, which concurrently hindered efforts to retrace transmission pathways and perpetuated the spread of the virus. As a result, by Mar. 11, 2020, mere months after emergence of the disease, the World Health Organization had already characterized COVID-19 as a pandemic.

SUMMARY

The disclosure provides methods and systems for multiplex viral detection using monodisperse emulsion droplets and template particles. The methods and systems allow for the detection of one or more viruses in a sample using a sequencing-based approach while obviating the need for complex microfluidics. Methods and systems of the disclosure generate an emulsion with template particles to segregate viral nucleic acids into monodisperse droplets. This approach provides a massively parallel, analytical workflow for detecting the presence of one or more viruses in a sample that is inexpensive, scalable, and accurate, while eliminating many of the drawbacks associated with existing viral detection modalities.

Methods and systems of the disclosure make use of template particles that serve as templates for making a large number of monodisperse emulsion droplets simultaneously in a single tube or vessel. By adding a plurality of template particles into an aqueous mixture, layering oil over the aqueous phase, and vortexing or shaking the tube, the particles serve as templates while the shear force of the vortexing or shaking causes the formation of water-in-oil monodisperse droplets with one particle in each droplet.

Methods and systems of the disclosure provide template particles that capture the nucleic acids of virus particles from a sample. The template particles with captured nucleic acids are segregated simultaneously into monodisperse emulsion droplets with a single template particle and its captured viral nucleic acids in each droplet. Methods further include sequencing the viral nucleic acids segregated in the droplets. Data generated by sequencing the viral nucleic acids allows for detection and identification of the captured viral particles and can, for example, be used to make a diagnosis or track the spread of a virus in a population.

Methods and systems of the disclosure provide template particles that capture individual virus particles from a sample. Template particles may be configured to capture a particular virus or viruses. Methods and systems of the disclosure provide a plurality of capture particles configured to capture different viruses. The template particles with captured virus particles are segregated simultaneously into monodisperse emulsion droplets with a single template particle and single virus particle in each droplet. The nucleic acids of individual virus particles are then released into the droplets in which the virus particles were segregated. The template particles may also capture the released nucleic acids. Methods further include sequencing the viral nucleic acids segregated in the droplets. Data generated by sequencing the viral nucleic acids allows for detection and identification of the captured viral particles and can, for example, be used to make a diagnosis or track the spread of a virus in a population.

Viral nucleic acids segregated in monodisperse emulsion droplets may be barcoded. The barcoded viral nucleic acids may be amplified to generate a plurality of barcoded amplicons that can be traced back to a template particle that was segregated with the viral nucleic acids in a monodisperse emulsion droplet. The plurality of barcoded amplicons may be sequenced by, for example, next-generation sequencing methods to generate sequence reads. Methods may further include processing the sequence reads to, for example, determine the identity of a virus from a sample.

Methods and systems of the disclosure can be used to detect and identify viruses having DNA or RNA genomes. With a non-limiting reference to the Baltimore Classification System, as explained in Mahmoudabadi and Phillips, eLife, 2018 (7): e31955, the methods and systems of the disclosure can be used to detect and identify double-stranded DNA viruses (Group I), single-stranded DNA viruses (Group II), double-stranded RNA viruses (Group III), positive single-stranded RNA viruses (Group IV), negative single-stranded RNA viruses (Group V), positive single-stranded RNA viruses with DNA intermediates (Group VI), and double-stranded DNA retroviruses (Group VII).

Methods and systems of the disclosure can be used to detect and identify viruses having RNA genomes. These methods may further include reverse transcribing the viral genomic RNA segregated in the monodisperse emulsion droplets and sequencing the resulting cDNA. The resulting cDNA may be barcoded and amplified to generate a plurality of barcoded amplicons that can be traced back to a template particle that was segregated with the viral genomic RNA in a monodisperse emulsion droplet. The plurality of barcoded amplicons may be sequenced by, for example, next-generation sequencing methods to generate sequence reads. Methods may further include processing the sequence reads to, for example, determine the identity of a virus from a sample.

In certain aspects, the methods and systems of the disclosure provide a method for segregating viral nucleic acids into droplets. The droplets may be prepared as emulsions, e.g., as an aqueous phase fluid dispersed in an immiscible phase carrier fluid (e.g., a fluorocarbon oil, silicone oil, or a hydrocarbon oil) or vice versa. Generally, the droplets are formed by shearing two liquid phases. Shearing may comprise any one of vortexing, shaking, flicking, stirring, pipetting, or any other similar method for mixing solutions. Methods of the invention include combining virus particles or viral nucleic acids with template particles in a first fluid, adding a second fluid, and shearing or agitating the first and second fluid. Preferably, the first fluid is an aqueous phase fluid, and, in some embodiments, may comprise reagents selected from, for example, buffers, salts, divalent cations (e.g., $Mn^{2+}$ and/or $Mg^{2+}$), lytic enzymes (e.g. proteinase k) and/or other lytic reagents (e.g., Triton X-100, Tween-20, Tween-80, IGEPAL, or combinations thereof), nucleic acid synthesis reagents e.g., nucleic acid amplification reagents or reverse transcription mix, or combinations thereof.

Methods and systems of the disclosure use template particles to template the formation of monodisperse droplets and isolate viral particles and/or viral nucleic acids. Template particles according to aspects of the invention may comprise hydrogel, for example, selected from agarose, alginate, a polyethylene glycol (PEG), a polyacrylamide (PAA), acrylate, acrylamide/bisacrylamide copolymer matrix, azide-modified PEG, poly-lysine, polyethyleneimine, and combinations thereof. In certain instances, template particles may be shaped to provide an enhanced affinity for viruses or a particular group of viruses, e.g., a viral family, genus, group, class, or species. For example, the template particles may be generally spherical but the shape may contain features such as flat surfaces, craters, grooves, protrusions, and other irregularities in the spherical shape that promote an association with a virus such that the shape of the template particle increases the probability of templating a droplet that contains the a virus.

In some aspects, methods and systems of the disclosure provide template particles that include one or more internal compartments. The internal compartments may contain a reagent and/or compound that is releasable upon an external stimulus. Reagents contained by the template particle may include, for example, cell lysis reagents or nucleic acid synthesis reagents (e.g., a polymerase). The external stimulus may be heat, osmotic pressure, or an enzyme. For example, in some instances, methods of the invention include releasing a reverse transcriptase directly inside of a droplet containing viral genomic RNA. A plurality of different template particles configured to capture different viruses may contain different reagents and/or compounds. Such different template particles may release their different reagents and/or compounds upon a different type or degree of external stimulus.

In some aspects, methods and systems of the invention include lysing viral particles to release viral nucleic acids. Methods include capturing virus particles with template particles and segregating the template particles with captured viral particles simultaneously into monodisperse emulsion droplets with a single template particle and single virus particle in each droplet, and lysing the virus particles to release viral nucleic acids. Methods include lysing virus particles to release viral nucleic acids, capturing viral nucleic acids with a template particle, and segregating the template particles with capture viral nucleic acids simultaneously into monodisperse droplets having a single template particle in each droplet. The released viral nucleic acids may be fragmented, and fragmentation may occur concurrently with lysing the virus particles. Lysing and fragmentation may be accomplished using mechanical, chemical, or enzymatic means, the addition of heat, divalent cations (e.g., $Mn^{2+}$ and/or $Mg^{2+}$), or a combination thereof.

In certain aspects, this disclosure provides a kit for detecting one or more viruses in a sample. The kit includes one or more types of template particles configured to capture different types of virus particle. A researcher following instructions provided by the kit can use template particles to determine the presence or identity of one or more viruses in a sample. The template particles may be shipped inside sample preparation tubes, or sample collection tubes, such as, blood, sputum, and buccal swab collection tubes. The template particles are preferably in a dried format. The kit may further include reagents, such as, cell lysis reagents, and nucleic acid synthesis reagents.

An insight of the disclosure is that a plurality of droplets can be made in a single tube at a temperature and/or at a mixing speed. For example, by mixing at about 50 degrees C. and/or at about 500 rpm, methods can successfully, in the single tube, form the droplets that contain the template particles and captured virus particles or virus nucleic acids thereby isolated into individual aqueous partitions. Thus, methods of the disclosure provide important tools for basic biology, clinical research, and patient testing.

In some embodiments, the vortexing is performed on a vortexing instrument, e.g., which vortexes the mixture at a suitable rate such as between about two hundred and about seven hundred rpm (preferably about 500 rpm). The vortexing instrument may include a heater that heats the mixture during vortexing. The mixture may be pre-prepared with a plurality of template particles at a number to capture a suitable target number of virus particles or viral nucleic acids. For example, the mixture may initially include thousands, tens of thousands, hundreds of thousands, millions, or at least about 10 million template particles.

Each of the particles may contain some of the reagents used, for example, in reverse transcribing viral RNA, lysing virus particles, and/or preparing amplicons from viral nucleic acids. Preferably, each of the particles serves as a template to initiate formation of aqueous monodisperse droplets in oil, in which each droplet comprises one particle. The particles may be hydrogel particles and may include, for example, polyacrylamide (PAA) or polyethylene glycol (PEG).

Preferably the aqueous mixture includes a plurality of template particles, and shaking the sample vessel causes each template particle to serve as a template in the formation of one of the droplets. The nucleic acids may initially be in virus particles and the shaking step may cause droplets to form such that each of the droplet contains one template particle and one or virus particles. The method may include lysing the virus particles within the droplets to release the nucleic acids into the droplets and the method may include, during the shaking step, heating the aqueous mixture to a temperature that promotes reverse transcription.

BRIEF DESCRIPTION OF THE DRAWINGS

FIG. 10 shows amplicons and primers according to certain methods of the disclosure.

FIG. 11 shows amplicons and primers according to certain methods of the disclosure.

DETAILED DESCRIPTION

Figure 1:
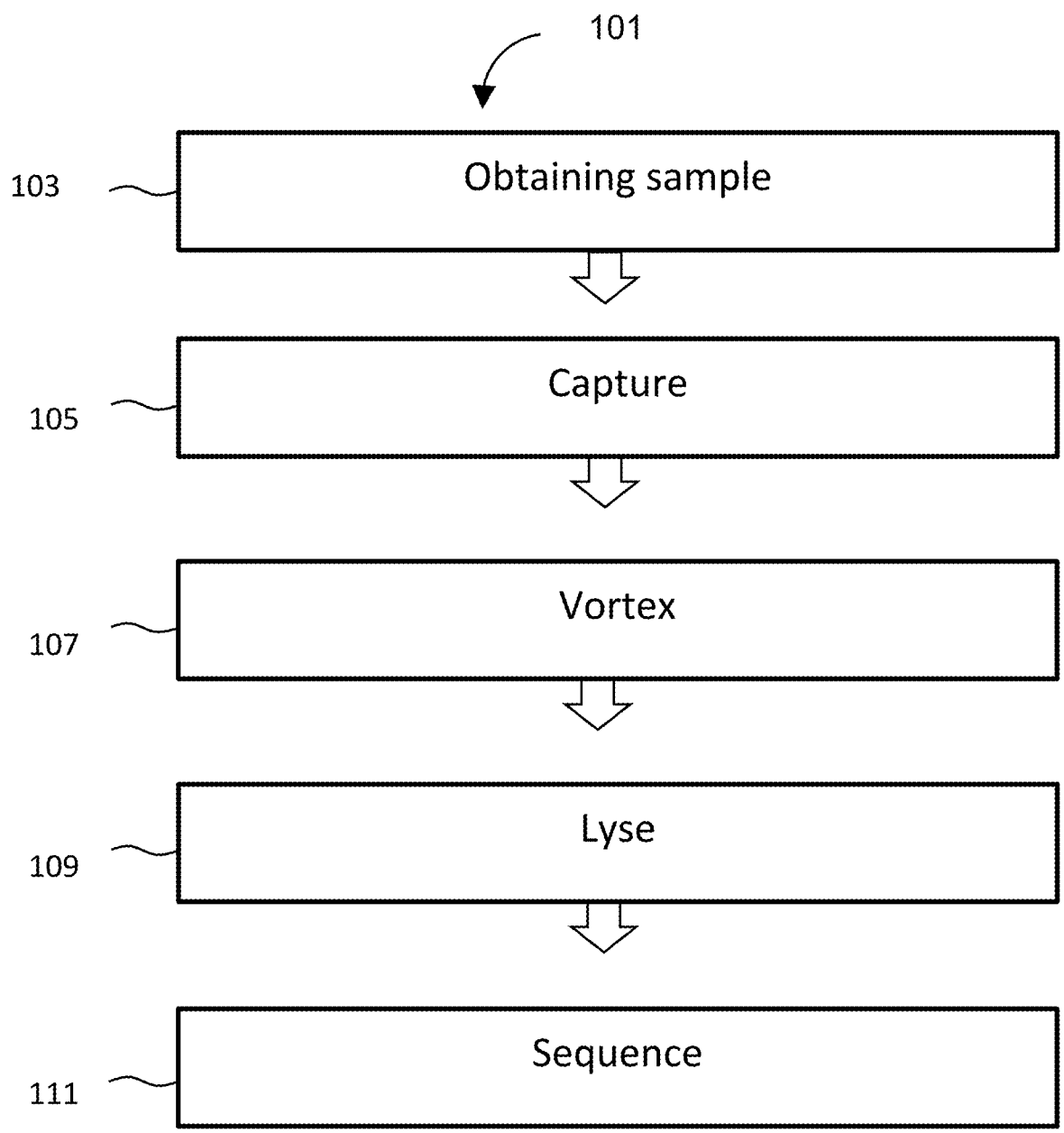
FIG. 1 diagrams a method for sequencing viral nucleic acid from a sample.

The disclosure generally relates to methods and systems for multiplex viral detection using fluid partitions (e.g., droplets) that isolate viral nucleic acids in the partitions for subsequent sequencing. The methods and systems use pre-made particles, such as hydrogel particles, that serve as templates and cause water-in-oil emulsion droplets to form when mixed in water with oil and vortexed or sheared. For example, an aqueous mixture can be prepared in a reaction tube that includes template particles and viral particles or viral nucleic acids in aqueous media (e.g., water, saline, buffer, etc.). An oil is added to the tube, and the tube is agitated (e.g., on a vortex mixer, aka vortexer). The template particles act as templates in the formation of monodisperse droplets that each contain one template particle, with a captured viral particle or viral nucleic acids, in an aqueous droplet surrounded by the oil. The methods and systems allow for the detection of one or more viruses in a sample using a sequencing-based approach while obviating the need for complex microfluidics. This approach provides a massively parallel analytical workflow for detecting the presence of one or more viruses in a sample that is inexpensive, scalable, and accurate, while eliminating many of the drawbacks associated with existing viral detection modalities.

The methods and systems of the disclosure leverage the particle-templated emulsification technology described in Hatori et. al., Anal. Chem., 2018 (90): 9813-9820, which is incorporated by reference. Essentially, micron-scale beads (such as hydrogels) or "template particles" are used to define an isolated fluid volume surrounded by an immiscible partitioning fluid and stabilized by temperature insensitive surfactants.

Methods and systems of the disclosure make use of template particles that serve as templates for making a large number of monodisperse emulsion droplets simultaneously in a single tube or vessel. By adding a plurality of template particles into an aqueous mixture, layering oil over the aqueous phase, and vortexing or shaking the tube, the particles serve as templates while the shear force of the vortexing or shaking causes the formation of water-in-oil monodisperse droplets with one particle in each droplet.

The droplets all form at the moment of vortexing-essentially instantly as compared to the formation of droplets by flowing two fluids through a junction on a microfluidic chip. Each droplet thus provides an aqueous partition, surrounded by oil. An important insight of the disclosure is that the particles can be provided with reagents that promote useful biological reactions in the droplets and even that reverse transcription can be initiated during the mixing process that causes the formation of the partitions around the template droplets.

Methods and systems of the disclosure provide template particles that capture individual virus particles from a sample. Template particles may be configured to capture particular viruses or a particular virus. Methods and systems of the disclosure provide a plurality of capture particles configured to capture different viruses. The template particles with captured virus particles are segregated simultaneously into monodisperse emulsion droplets with a single template particle and single virus particle in each droplet. The nucleic acids of individual virus particles are then released into the droplets in which the virus particles were segregated. The template particles may also capture the released nucleic acids. Methods further include sequencing the viral nucleic acids segregated in the droplets. Data generated by sequencing the viral nucleic acids allows for detection and identification of the captured viral particles and can, for example, be used to make a diagnosis or track the spread of a virus in a population.

FIG. 1 diagrams a method 101 for determining the sequence of a virus in a sample. The method 101 includes obtaining a sample 103. Obtaining 103 may include taking blood, plasma, serum, urine, saliva, tear fluid, seminal fluid, a vaginal swab, a nasal swab, a rectal swab, a skin swab, an in ear swab, a cheek swab, a throat swab, a faecal sample, and the like. As explained in Niedgrig et al., BMC Infect Dis, 18, 707 (2018), which is incorporated by reference, viral presence and concentrations in a sample depend on virus type and sample type. For example, as explained in Ali et al., Virol J, 12, 178 (2015), for common respiratory viruses such as rhinovirus, coronavirus, and influenza, nasal or throat swabs provide samples with detectable virus particles. The samples may be processed or cultivated to concentrate viral particles.

Viral particles from the sample are captured 105 by template particles in a first fluid in a vessel, to which a second fluid that is immiscible with the first fluid is added. The first fluid is preferably an aqueous fluid. The vessel may be a tube. The tube can be any type of tube, such as a sample preparation tube sold under the trade name Eppendorf, or a blood collection tube, sold under the trade name Vacutainer. Template particles may be in dried format. Methods may include pipetting a sample comprising virus particles and, for example, the aqueous fluid into the tube containing template particles and then adding a second fluid that is immiscible, such as oil.

The method 101 then includes vortexing 107 the fluids to generate monodisperse droplets, i.e., droplets. Preferably, vortexing comprises pushing a tube containing the fluid onto a vortexer. After vortexing 107, a plurality (e.g., thousands, tens of thousands, hundreds of thousands, one million, two million, ten million, or more) of aqueous partitions is formed essentially simultaneously. Vortexing causes the fluids to partition into a plurality of monodisperse droplets. A substantial portion of droplets will contain a single template particle and a single viral particle. Droplets containing more than one or none of a template particle or virus particle can be removed, destroyed, or otherwise ignored.

The next step of the method 101 is to lyse 109 the viral particles in the monodisperse droplets to release viral nucleic acids. Lysis 109 may be induced by a stimulus, such as, for example, lytic reagents, detergents, enzymes, mechanical stimulus, divalent cations, heat, or a combination thereof. Reagents, detergents, enzymes, and cations to induce cell lysis may be provided by the template particles via internal compartments. In some embodiments, lysing 109 involves heating the monodisperse droplets to a temperature sufficient to release lytic reagents contained inside the template particles into the monodisperse droplets. The released viral nucleic acids may be fragmented, and fragmentation may occur concurrently with lysing 109 the virus particles. Lysing 109 and fragmentation may be accomplished using mechanical, chemical, or enzymatic means, the addition of heat, divalent cations (e.g., $Mn^{2+}$ and/or $Mg^{2+}$), or a combination thereof.

After lysing 109, the released viral nucleic acid may be sequenced 111. Prior to sequencing 111, the viral nucleic acid segregated in monodisperse emulsion droplets may be barcoded. The barcoded viral nucleic acids may be amplified to generate a plurality of barcoded amplicons that can be traced back to a template particle that was segregated with the viral nucleic acids in a monodisperse emulsion droplet. If a captured virus particle has an RNA-based genome, the released viral nucleic acids may undergo reverse transcription and barcoding to create barcoded cDNA, the barcoded cDNA may be amplified to generate a plurality of barcoded amplicons. The plurality of barcoded amplicons may be sequenced 111 by, for example, next-generation sequencing methods to generate sequence reads. Methods may further include processing the sequence reads to, for example, determine the identity of a virus from a sample.

Advantageously, by isolating a single viral particle in a single droplet, sequencing 111 generates reads specific to a particular virus particle, without interference or contamination from other nucleic acids. Further, certain viruses have segmented genomes comprising physically disconnected molecules. This can impede conventional short read sequencing as it can be difficult to associate reads from the disconnected molecules. By ensuring that all portions of a segmented genome are contained within a single droplet, this problem is obviated. An additional advantage conferred isolating a single virus particle in a single droplet is that an intrinsic viral titer is formed from a sample, and the uniquely captured virus particles can be counted directly from the number of isolated virus particles sequenced. This can be accomplished, for example, by counting sequence reads associated with unique droplets.

Figure 2:
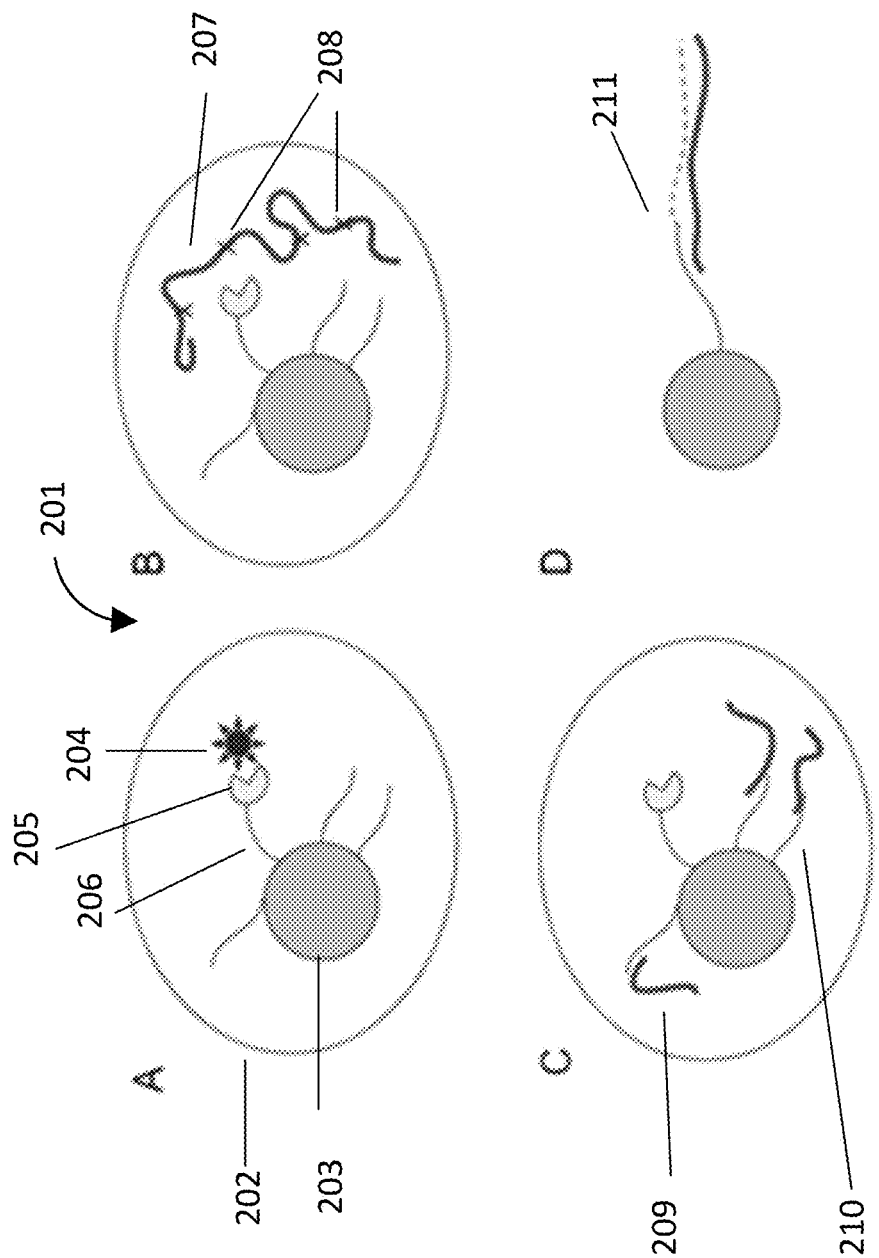
FIG. 2 shows a schematic for segregating viral nucleic acid from a sample.

FIG. 2 shows a non-limiting schematic 201 of a portion of the method 101 from FIG. 1. In FIG. 2A, a single virus particle 204 is captured by capture moiety 204 tethered to a single template particle 203. The capture moiety 204 may be, for example, an antibody specific to virus or viruses. The capture moiety 204 is tethered to the template particle 203 by a linkage 206. The template particle 203 with captured virus particle 204 is segregated within a monodisperse emulsion droplet 202 by vortexing 107. The captured virus particle is lysed 109 to release viral nucleic acid. In FIG. 2B, the released viral nucleic acid 207 is segregated within the emulsion droplet 202. The viral nucleic acid 207 can be fragmented. This may occur during lysis 109 of the virus particle. Each "X" on the viral nucleic acid 207 represents a location in which the nucleic acid was fragmented 208. In FIG. 2C, the fragmented viral nucleic acid 209 is captured by capture probes 210 attached to the template particle 203. The capture probes may comprise a primer, a template particle specific barcode sequence, and/or a capture sequence such as a random hexamer. If the virus particle 204 has an RNA genome, the fragmented viral nucleic acid 209 may undergo reverse transcription. In FIG. 2D, the cDNA product 211 of reverse transcription is shown. The viral nucleic acids or amplicons thereof are sequenced 111.

Figure 3:
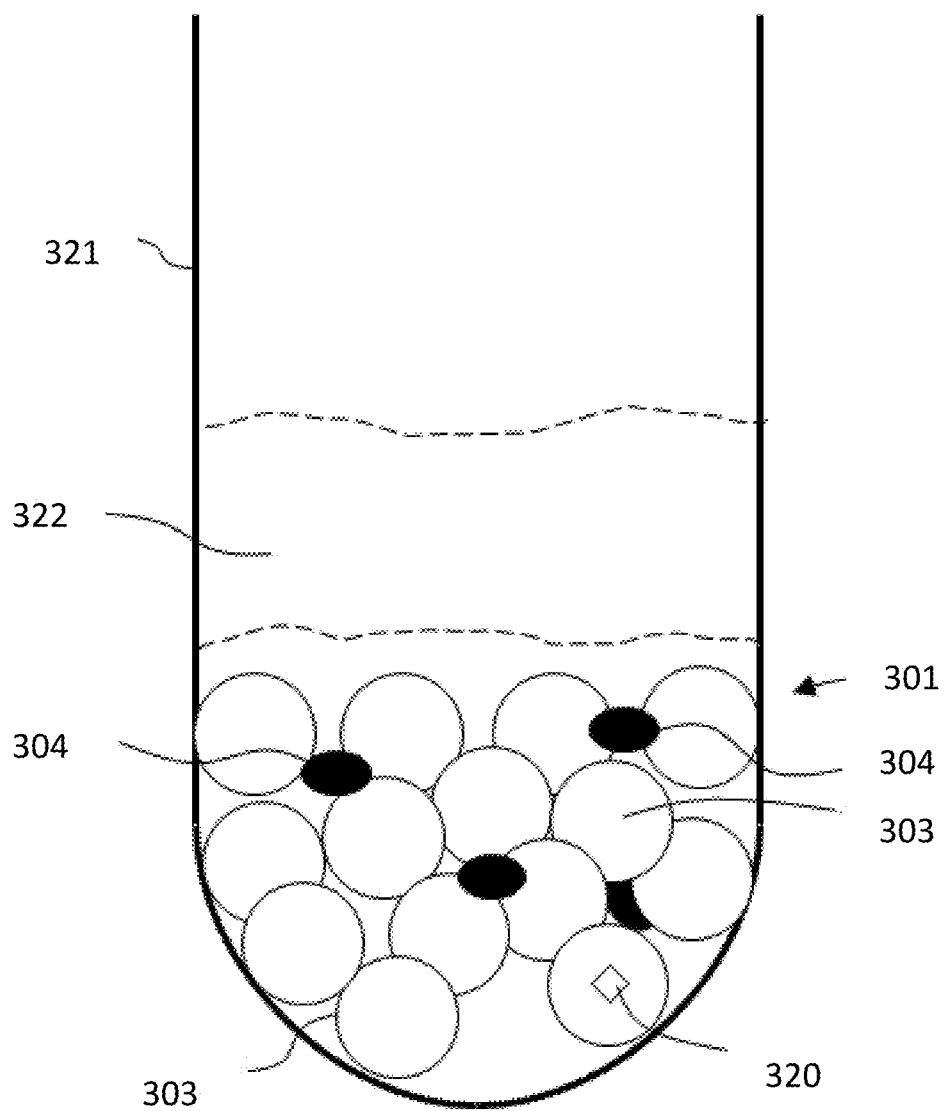
FIG. 3 shows a sample with template particles and virus particles.

FIG. 3 shows a mixture 301 that includes virus particles 304 and reagents 320, for example, those required for reverse transcription of viral RNA to cDNA. As shown, the mixture 301 is provided in a sample vessel 321 or tube. The tube includes template particles 303 that will capture the virus particles 304 and serve as templates in the creation of the monodisperse emulsion droplets. The reagents 320 may be provided by various methods or in various formats. In the depicted mixture 301, the reagents 320 are provided by the template particles 303. When using template particles 303 of a certain structure, such as hydrogels, the reagents 320 may be enclosed within, embedded with, stuck to, or linked to the template particles 303. As shown, the template particles 303 and the virus particles 304 are in an aqueous mixture 301. The method 301 may include adding an oil 322 onto the mixture 301 prior to any vortexing 107. It may be preferable to use a fluorinated oil for the oil 322, and a surfactant such as a fluorosurfactant may also be added (separately, or with the oil 322, or with the aqueous mixture 301). See Hatori, 2018, Particle-templated emulsification for microfluidics-free digital biology, Anal Chem 90:9813-9820, incorporated by reference. It may be found that aqueous-soluble surfactants promote formation of monodisperse (each droplet has one template particle) droplets. Preferred materials for the template particles 303 include hydrogels such as polyacrylamide (PAA) and PEG. In one a non-limiting example, the sample vessel 321 includes PAA particles 303 with 0.5% Triton suspended in 1.25 volume of HFE oil 322 with 2% (20 μL) or 5% (200 μL and 2 mL) fluorosurfactant. Once the aqueous mixture 301 is prepared, the mixture is vortexed.

Figure 4:
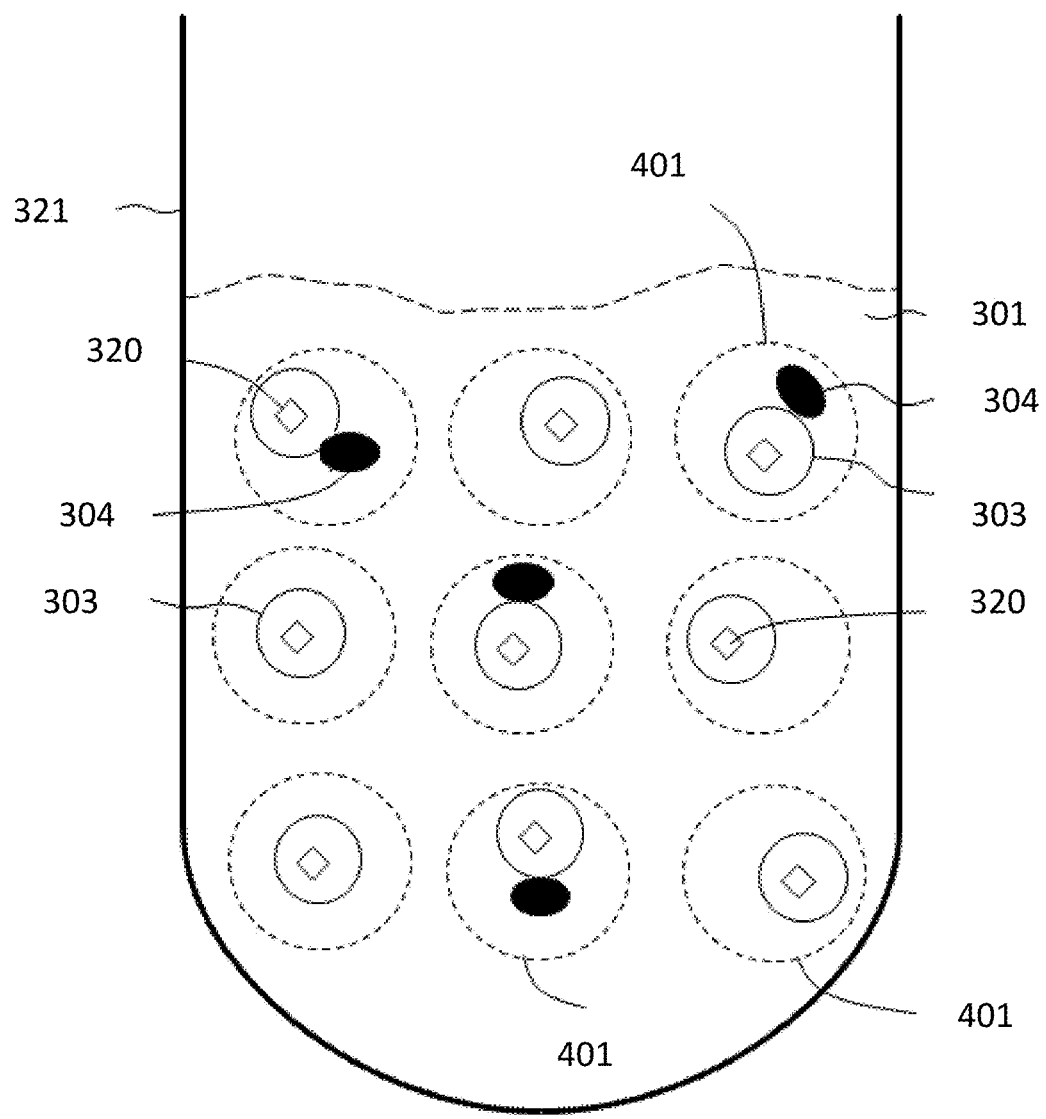
FIG. 4 shows the droplets formed during vortexing according to certain methods of the disclosure.

FIG. 4 shows the monodisperse emulsion droplets 401 formed during vortexing 107. During the vortexing 107, the template particles 303 template the formation of the droplets 401. The template particles 303 and/or the mixture 301 may include reagents 320 such as those that promote reverse transcription of viral RNA. For example, where the template particles 303 are hydrogels having reagents embedded or enclosed therein, the particles may release reagents 320 into the droplets 401 as the droplets form. The template particles may release the reagents as a natural consequences of forming the aqueous mixture 301 and vortexing 107 (e.g., due to osmotic or phase changes associated with introduction of an aqueous fluid, the sample, or via salts that are introduced to influence osmotic/tonic conditions. The reagents may be released by stimulus (e.g., sonication, heat, or the vortexing 107 itself). The reagents may migrate electrophoretically from the template particles 303 into the surrounding aqueous media under the influence of electrostatic charge (e.g., self-repulsion out of the particles).

Some or all of the reagents may be provided in or with (embedded within or surface-linked to) the template particles 304 while additional or alternatively some or all of the reagents may be separately added to the sample vessel 321. For example, certain molecular reagents such as polymerase enzymes are packaged in the particles, some reagents such as oligonucleotides are linked (e.g., covalently) to the particles, and some reagents such as lysis agents (e.g., detergent), dNTPs, and metal ions are added independently.

Vortexing 107 causes the fluids to partition into a plurality of monodisperse emulsion droplets 401. A substantial portion of droplets will contain a single template particle 303 and a single captured virus particle 304. Droplets containing more than one or none of a template particle or virus particle can be removed, destroyed, or otherwise ignored. Droplets formed according to methods of the disclosure are monodisperse meaning that the vast majority of the droplets 401 will include one template particle 303 and the vast majority of template particles 303 will form into one droplet 401. Said another way, monodisperse means that comparing the number of template particles 303 initially provided in the aqueous mixture 301 to the number of droplets 401 produced by vortexing, the smaller number will be at least 90% of the larger number, and in practice usually at least 95%, more preferably 98% or 99%.

Figure 5:
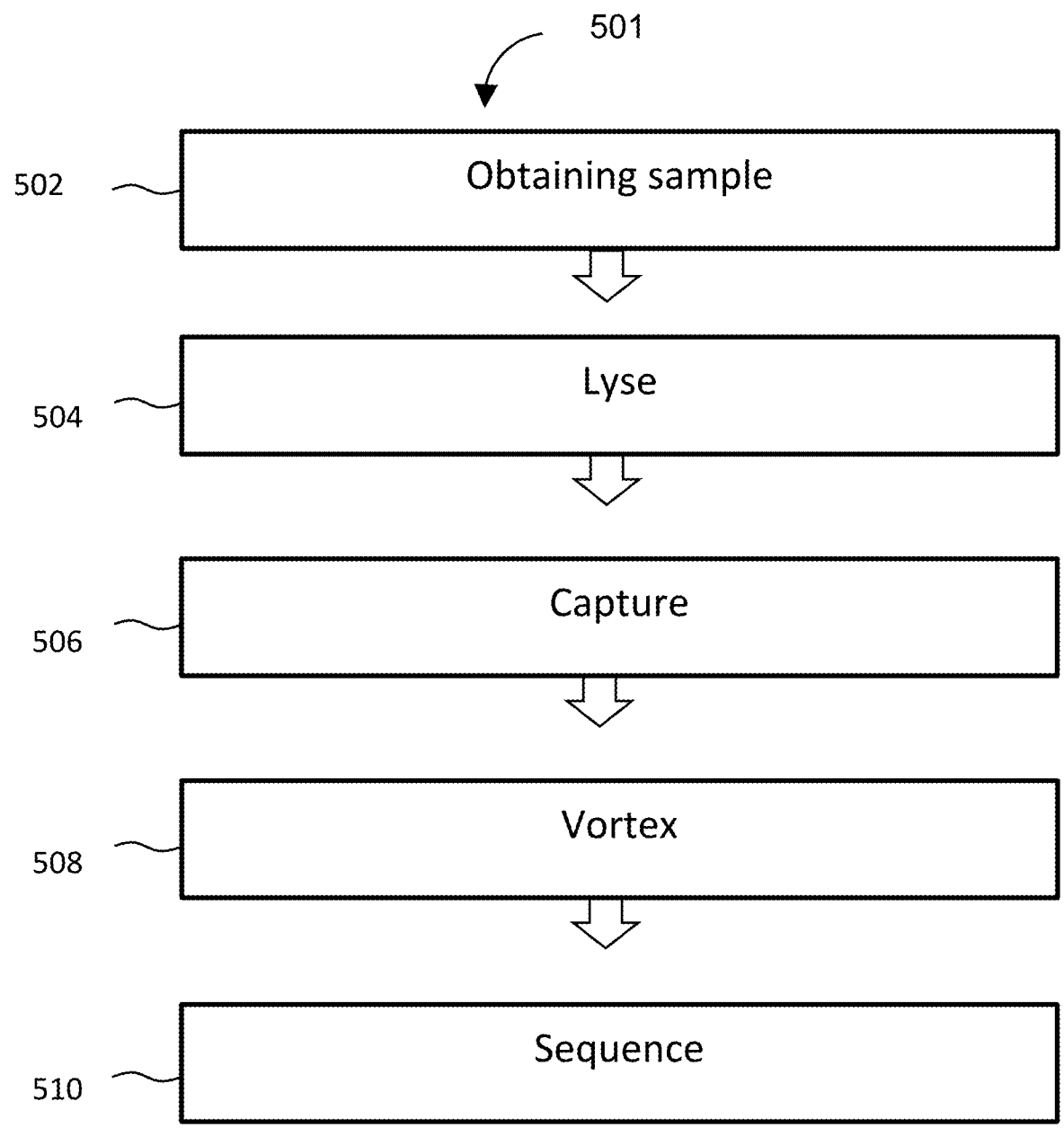
FIG. 5 shows a schematic for segregating viral nucleic acid from a sample.

FIG. 5 diagrams a method 501 for determining the sequence of a virus in a sample. The method 501 includes obtaining a sample 502. Obtaining 502 may include taking blood, plasma, serum, urine, saliva, tear fluid, seminal fluid, a vaginal swab, a nasal swab, a rectal swab, a skin swab, an in ear swab, a cheek swab, a throat swab, a fecal sample, and the like. Advantageously, the methods and systems of the disclosure may be used to determine the sequence of a virus directly from a sample, sometimes following a dilution or resuspension of the sample. However, in some instances the samples may be processed or cultivated to concentrate viral particles using known methods.

The next step of the method 501 is to lyse 504 the viral particles from a sample to release viral nucleic acids. Lysis 504 may be induced by a stimulus, such as, for example, lytic reagents, detergents, enzymes, mechanical stimulus, divalent cations, heat, or a combination thereof. The released viral nucleic acids may be fragmented, and fragmentation may occur concurrently with lysing 504 the virus particles. Lysing 504 and fragmentation may be accomplished using mechanical, chemical, or enzymatic means, the addition of heat, divalent cations (e.g., $Mn^{2+}$ and/or $Mg^{2+}$), or a combination thereof.

Viral nucleic acids from the sample are captured 506 by template particles in a first fluid in a vessel, to which a second fluid that is immiscible with the first fluid is added. The first fluid is preferably an aqueous fluid. The vessel may be a tube. The tube can be any type of tube, such as a sample preparation tube sold under the trade name Eppendorf, or a blood collection tube, sold under the trade name Vacutainer. Template particles may be in dried format. Methods may include pipetting a sample comprising viral nucleic acids and, for example, the aqueous fluid into the tube containing template particles and then adding a second fluid that is immiscible, such as oil.

The method 501 then includes vortexing 508 the fluids to generate monodisperse droplets, i.e., droplets. Preferably, vortexing comprises pushing a tube containing the fluid onto a vortexer. After vortexing 508, a plurality (e.g., thousands, tens of thousands, hundreds of thousands, one million, two million, ten million, or more) of aqueous partitions is formed essentially simultaneously. Vortexing 508 causes the fluids to partition into a plurality of monodisperse droplets. A substantial portion of droplets will contain a single template particle with captured viral nucleic acids. Droplets containing more than one or none of a template particle can be removed, destroyed, or otherwise ignored.

After vortexing 508, the viral nucleic acid may be sequenced 510. Prior to sequencing 510, the viral nucleic acid segregated in monodisperse emulsion droplets may be barcoded. The barcoded viral nucleic acids may be amplified to generate a plurality of barcoded amplicons that can be traced back to a template particle that was segregated with the viral nucleic acids in a monodisperse emulsion droplet. If captured viral nucleic acids are RNA, the released viral nucleic acids may undergo reverse transcription and barcoding to create barcoded cDNA. The barcoded cDNA may be amplified to generate a plurality of barcoded amplicons. The plurality of barcoded amplicons may be sequenced 510 by, for example, next-generation sequencing methods to generate sequence reads. Methods may further include processing the sequence reads to, for example, determine the identity of a virus from a sample.

Figure 6:
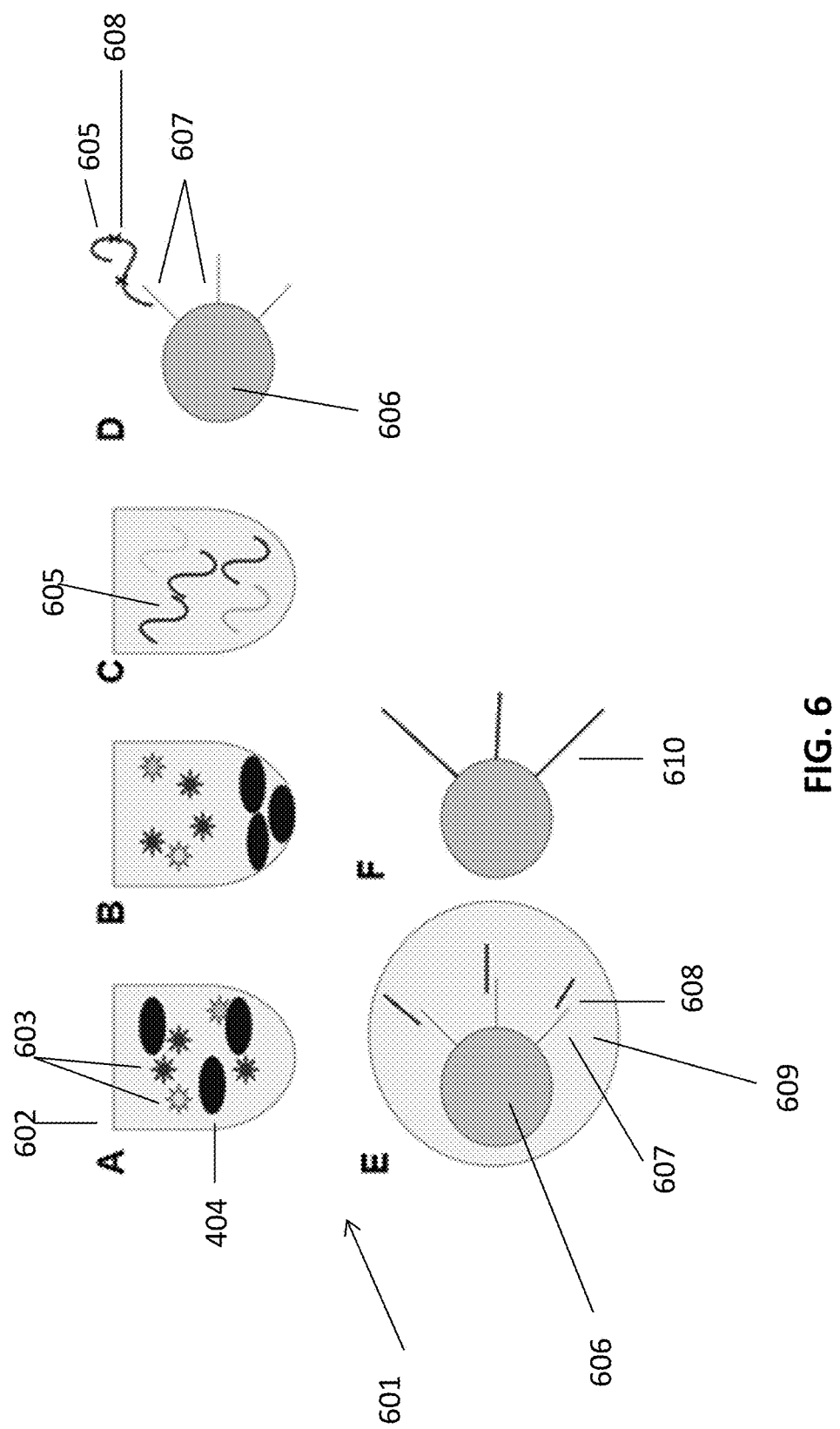
FIG. 6 shows a schematic for segregating viral nucleic acid from a sample.

FIG. 6 shows a non-limiting schematic 601 of a portion of the method 501 from FIG. 5. In FIG. 6A, a sample 602 is obtained, which comprises virus particles 603. The sample may also comprise cells and other large debris 604. FIG. 6B shows that the sample may be processed, e.g., diluted and/or centrifuged to remove cells and other large debris. In FIG. 6C the virus particles are lysed and release viral nucleic acids 605. Template particles and the viral nucleic acids are combined in a fluid, which is generally an aqueous fluid. In FIG. 6D, a viral nucleic acid 605 is captured by capture probes 607 attached to a template particle 606. The viral nucleic acid may be fragmented. Each "X" on the viral nucleic acid 605 represents a fragmentation site 608. A second fluid immiscible with the first fluid is added to the first fluid containing the template particle 606 with captured viral nucleic acid 605, and subsequently vortexed or sheared. This causes the fluids to partition into a plurality of monodisperse emulsion droplets that each contain a single template particle with an attached viral nucleic acid. FIG. 6E shows a template particle 606 with fragmented viral nucleic acids 608 captured by capture probes 607 attached to the template particle 606. The template particle 606 is segregated in a monodisperse emulsion droplet 609. The capture probes 607 may comprise a primer, a template particle specific barcode sequence, a unique molecule identifier (UMI) and/or a capture sequence such as a random hexamer. If the fragmented viral nucleic acids 608 are RNA, the fragmented viral nucleic acid 608 may undergo reverse transcription. In FIG. 6F, the cDNA product 610 of reverse transcription is shown.

In the methods of the disclosure vortexing may be accomplished by any suitable method or mechanism. The mixture may be contained in a tube such as a microcentrifuge tube. The tube may be manually flicked, or pressed down on a benchtop vortexer. The mixture may be in a well in a plate, such as a 96-well plate, and the plate may be loaded onto a benchtop mixer or shaker. The mixture may be in one tube of an 8-tube strip of microcentrifuge tubes such as the 8-tube strip sold under the trademark EPPENDORF. In a preferred embodiment, the tube is loaded into a vortexing instrument.

Methods and systems of the disclosure may include preparing a cDNA library from viral genomic RNA. Many disease-causing viruses in humans have RNA viruses, for example, coronavirus, influenza, rhinovirus, orthopneumovirus, parainfluenza viruses, and human metapneumovirus. Creating such a cDNA library may facilitate sequencing viral genomic RNA. For example, a sample that includes one or more virus particles may be mixed with template particles to form a partition (e.g., droplet) that includes a single virus particle in each droplet. The virus particle can be lysed and viral RNAs can be reverse transcribed into cDNAs in the droplet during the mixing stage that forms the partitions. Similarly, a sample that includes virus particle-free RNA can be mixed with oligo-linked template particles and mixed (e.g., shaken, vortexed, or sheared) to form droplets while simultaneously beginning to transcribe the RNA to cDNA. Whether starting with whole virus particles or virus particle-free RNA, the result is the formation of droplets that include cDNA copies of the starting RNA. Because the cDNA is more stable than viral RNA (e.g., cDNA does not include 2' hydroxyl groups that autocatalyze the molecule's own hydrolysis), the droplets provide a stable cDNA library that may be used in downstream assays to study the viral RNA content of the starting sample.

Forming the cDNAs while initially forming the droplets avoids problems caused by the ephemeral nature of viral RNA. Sample preparation and library preparation methods of the disclosure improve the ability of laboratory techniques to study viral RNA compositions of a sample.

Template particles of the disclosure may be made of any suitable material such as, for example, polyacrylamide, poly (lactic-co-glycolic acid), polyethylene glycol, agarose, or other such material. In some embodiments, hydrogel particles are prepared. In some embodiments, 6.2% acrylamide (Sigma-Aldrich), 0.18% N,N'-methylene-bis-acrylamide (Sigma-Aldrich), and 0.3% ammonium persulfate (Sigma-Aldrich) are used for PAA particle generation. A total of 14% (w/v) 8-arm PEGSH (Creative PEGworks) in 100 mM NaHCO$_3$ and PEGDA (6 kDa, Creative PEGworks) in 100 mM NaHCO$_3$ may be used for PEG particle generation. A 1% low melting temperature agarose (Sigma-Aldrich) may be used for agarose particle generation. The agarose solution is warmed to prevent solidification. Agarose and PEG solutions are injected into a droplet generation device with the oil (HFE-7500 fluorinated oil supplemented with 5% (w/w) deprotonated Krytox 157 FSH) using syringe pumps (New Era, NE-501). The PAA solution is injected into the droplet generation device with the fluorinated oil supplemented with 1% TEMED. The hydrogel solution and oil are loaded into separate 1 mL syringes (BD) and injected at 300 and 500 µL, respectively, into the droplet generation device using syringe pumps. The PAA and PEG droplets are collected and incubated for 1 h at room temperature for gelation. The agarose droplets are incubated on ice for gelation. After gelation, the gelled droplets are transferred to an aqueous carrier by destabilizing them in oil with the addition of an equal volume of 20% (v/v) perfluoro-1-octanol in HFE-7500. The particles are washed twice with hexane containing 2% Span-80 (Sigma-Aldrich) to remove residual oil. Following the hexane wash, the particles are washed with sterile water until all oil is removed.

In preferred embodiments, template particles comprise a plurality of capture probes. Generally, the capture probe of the present disclosure is an oligonucleotide. In some embodiments, the capture probes are attached to the template particle's material, e.g., hydrogel material, via covalent acrylic linkages. In some embodiments, the capture probes are acrydite-modified on their 5' end (linker region). Generally, acrydite-modified oligonucleotides can be incorporated, stoichiometrically, into hydrogels such as polyacrylamide, using standard free radical polymerization chemistry, where the double bond in the acrydite group reacts with other activated double bond containing compounds such as acrylamide. Specifically, copolymerization of the acrydite-modified capture probes with acrylamide including a cross-linker, e.g. N,N'-methylenebis, will result in a crosslinked gel material comprising covalently attached capture probes. In some other embodiments, the capture probes comprise Acrylate terminated hydrocarbon linker and combining the said capture probes with a template particle will cause their attachment to the template particle. Template particles may also comprise one or more virus particle capture moieties. Virus particle capture moieties can be tethered to the template particles in a manner similar to the capture probes.

FIGS. 7-11 show an exemplary method of the disclosure using template particles comprising template probes to capture viral RNA.

Figure 7:
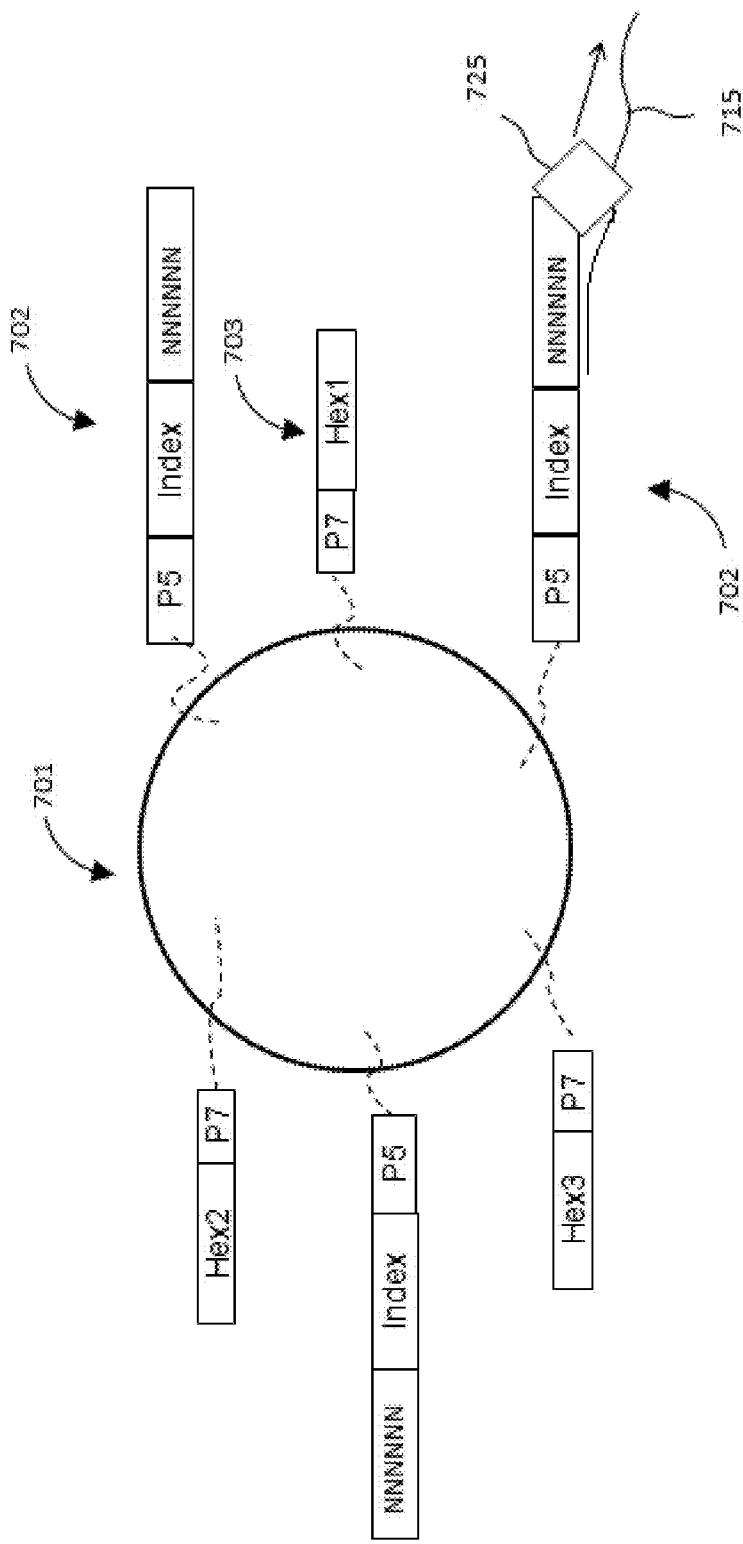
FIG. 7 is a schematic of a template particle according to certain embodiments.

FIG. 7 shows a template particle 701 linked to capture probes that can initiate reverse transcription of the viral RNA. As shown, the template particle 701 is linked to (among other things) viral RNA capture probes 702 that include a 3' random N-mer (although sequence-specific primers or random N-mers may be used). Random N-mers are preferably 6-12 nucleotides in length. Where the initial sample includes virus particle-free RNA, the capture probe hybridizes by Watson-Crick base-pairing to viral RNA in the sample and serves as a primer for reverse transcriptase, which makes a cDNA copy of the RNA. Where the initial sample includes intact virus particles (such as in methods using virus particle capture moieties 204), the same logic applies but the hybridizing and reverse transcription occurs once a virus particle releases RNA (e.g., by being lysed) in an emulsion droplet.

Methods of the disclosure may be used to make a cDNA library from viral RNA. The capture probes 702 may be used to at least synthesize a first cDNA copy of a viral RNA. The particles 701 may further include cDNA capture oligos 703 with 3' portions that hybridize to cDNA copies of the viral RNA. For the cDNA capture oligos, the 3' portions may include virus-specific sequences or hexamers. As shown, the capture probes 702 include, from 5' to 3', a binding site sequence P5, an index, and a random N-mer. The cDNA capture oligos include, from 5' to 3', a binding sequence P7 and a hexamer. Any suitable sequence may be used for the P5 and P7 binding sequences. For example, either or both of those may be arbitrary universal priming sequence (universal meaning that the sequence information is not specific to the naturally occurring genomic sequence being studied, but is instead suited to being amplified using a pair of cognate universal primers, by design). It is contemplated that the P5 sequences, the P7 sequence, and the index segment may be the sequences use in NGS indexed sequences such as performed on an NGS instrument sold under the trademark ILLUMINA, and as described in Bowman, 2013, Multi-plexed Illumina sequencing libraries from picogram quantities of DNA, BMC Genomics 14:466 (esp. in FIG. 2), incorporated by reference. The hexamer segments may be random hexamers or selective hexamers (aka not-so-random hexamers). The particle 701 is depicted as including 3 hexamer segments labelled Hex1, Hex2, and Hex3, but it will be appreciated that the particle 701 may be linked to many, e.g., thousands, of distinct hexamers. Hexamers are illustrated, but any suitable oligomers may be used. Preferred embodiments make use of not-so-random (NSR) oligomers (NSROs). See Armour, 2009, Digital transcriptome profiling using selective hexamer priming for cDNA synthesis, Nat Meth 6 (9): 647-650, incorporated by reference. Preferably, the particles 701 are linked to capture probes 702, 703 that include one or more primer binding sequences P5, P7 cognate to PCR primers that may be used in an option downstream amplifying step (such as PCR or bridge amplification).

The index segment may be any suitable barcode or index such as may be useful in downstream information processing. In preferred embodiments, the index for each capture probe is specific and unique to the template particle to which it is attached. The index may also contain a unique molecule identifier (UMI). The index or barcode may comprise any number of barcodes, index or index sequence, UMIs, which are unique, i.e., distinguishable from other barcode, or index, UMI sequences. The sequences may be of any suitable length which is sufficient to distinguish the barcode, or index, sequence from other barcode sequences. A barcode, or index, sequence may have a length of 4, 5, 6, 7, 8, 9, 10, 11, 12, 13, 14, 15, 16, 17, 18, 19, 20, 21, 22, 23, 24, 25 nucleotides, or more. In some embodiments, the barcodes, or indices, are pre-defined and selected at random.

In some methods of the invention, an index or barcode sequence may comprise unique molecule identifiers (UMIs). UMIs are a type of barcode that may be provided to a sample to make each nucleic acid molecule, together with its barcode, unique, or nearly unique. This may be accomplished by adding one or more UMIs to one or more capture probes of the present invention. By selecting an appropriate number of UMIs, every nucleic acid molecule in the sample, together with its UMI, will be unique or nearly unique.

UMIs are advantageous in that they can be used to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson et al., 2016, Counting Molecules in cell-free DNA and single cells RNA", Karolinska Institutet, Stockholm Sweden, incorporated herein by reference.

As shown, a capture oligo 701 hybridizes to a viral RNA 715. A fragmentation buffer may be added. A reverse transcriptase 725 binds and initiates synthesis of a cDNA copy of the viral RNA 715. Note that the viral RNA 715 is connected to the particle 701 non-covalently, by Watson-Crick base-pairing. The cDNA that is synthesized will be covalent linked to the particle 701 by virtue of the phosphodiester bonds formed by the reverse transcriptase 725.

Figure 8:
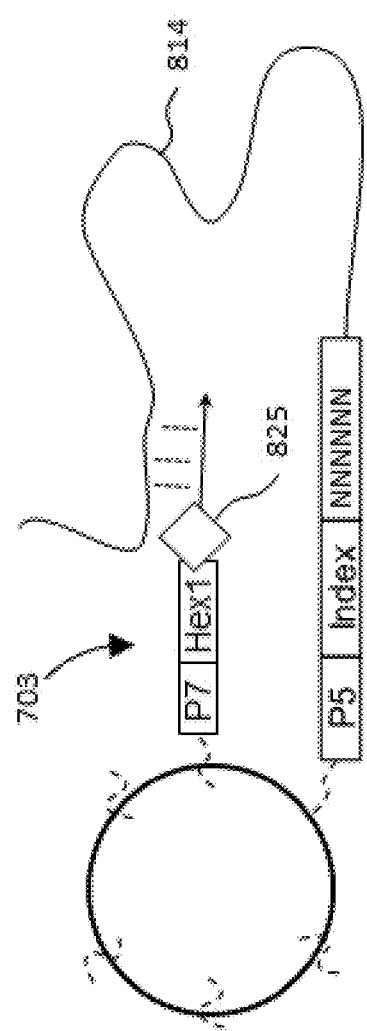
FIG. 8 is a schematic of a template particle according to certain embodiments.

FIG. 8 shows a cDNA 814 linked to a particle by virtue of its being a covalent, polymeric extension of the RNA capture probe 702. As shown, a 3' end of the cDNA capture oligo 703 will hybridize to the cDNA 814. A polymerase 825 will perform second-strand synthesis, copying the cDNA by extending the cDNA capture oligo 703.

Figure 9:
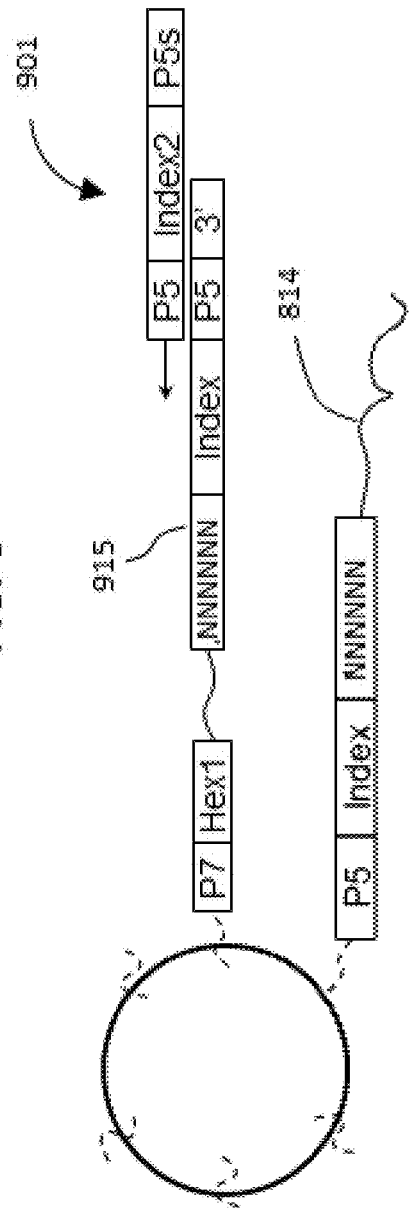
FIG. 9 is a schematic of a template particle according to certain embodiments.

FIG. 9 shows a first sense copy 915 of the cDNA 814. The first sense copy 915 is in the same sense as the viral RNA 715, both of which are antisense to the cDNA 814. At this stage, RNAse may be introduced to degrade the viral RNA 715. A free forward primer 901 is introduced that will hybridize to, and prime copying of, the first sense copy 915 of the cDNA 814.

FIG. 10 shows the antisense copy 914 that is made by extending the free forward primer 901. A free reverse primer 909 is introduced that hybridizes to the antisense copy 914. As shown, the free forward primer 901 and the free reverse primer 909 each have respective handles P5s and P7s. Those handles P5s, P7s may be any arbitrary sequence useful in downstream analysis. For example, they may be additional universal primer binding sites or sequencing adaptors. The free reverse primer 909 primers a polymerase-based synthesis of a sense copy 915 of the original viral RNA 715.

FIG. 11 shows the sense copy 915 of the original viral RNA 715. It may be appreciated that the free forward primer 901, the free reverse primer 909, the antisense copy 914, and the sense copy 915 provide the basis for performing an amplification reaction. It will be observed that copying the first sense copy 915 of the cDNA 814 using the free forward primer 901 is the first depicted step producing a molecular product not-covalently linked to the particle 213. Copying the sense copy 915 produces an antisense copy 914 that is not covalently linked to the particle 213. Of the sense copies 915, only the first sense copy 915 was covalently linked to the particle 213. After copying the first sense copy, every template has a barcode ("index"). This allows droplets to be broken, after which multiplexing can proceed in bulk aqueous phase. In fact, where multiple droplets were formed and used to perform reverse transcription, each template strand may be barcoded by droplet. After "breaking the emulsion" (releasing contents from droplets into bulk aqueous phase), the same free forward primer 901 and free reverse primer 909 may be used to amplify, in parallel and together, any number of sense copies 915 and antisense copies 914 (each barcoded back to original droplet and optionally to individual strand).

The terms "nucleic acid amplification reagents" or "reverse transcription mix" encompass without limitation dNTPs (mix of the nucleotides dATP, dCTP, dGTP and dTTP), buffer/s, detergent/s, or solvent/s, as required, and suitable enzyme such as polymerase or reverse transcriptase. The polymerase used in the disclosed methods may be a DNA polymerase, and may be selected from, but is not limited to, Taq DNA polymerase, Phusion polymerase, or Q5 polymerase. The reverse transcriptase used in the presently disclosed targeted library preparation method may be for example, Moloney murine leukemia virus (MMLV) reverse transcriptase, or maxima reverse transcriptase. In some embodiments, the general parameters of the reverse transcription reaction comprise an incubation of about 15 minutes at 25 degrees and a subsequent incubation of about 90 minutes at 52 degrees. Nucleic acid amplification reagents are commercially available, and may be purchased from, for example, New England Biolabs, Ipswich, MA, USA, or Clonetech.

According to aspects of the present disclosure, the term "universal primer sequence" generally refers to a primer binding site, e.g., a primer sequence that would be expected to hybridize (base-pair) to, and prime, one or more loci of complementary sequence, if present, on any nucleic acid fragment. In some embodiments, the universal primer sequences used with respect to the present methods are P5 and P7.

A person with ordinary skills in the art will appreciate that any one of the template particle embodiments, capture probes, primer probes, second strand primers, universal amplification primers, barcodes, UMIs, and methods thereof described in any one of the embodiments of the presently disclosed targeted library preparation method may be used in a different combination, or embodiment, of the present method. For example, any one of the presently described second strand primers, or primer probe, may be used to prime any one of the presently disclosed first strand to allow for a DNA synthesis reaction to generate an amplicon.

Embodiments of the disclosure may use the application of heat and/or divalent cations (e.g., $Mn^{2+}$ and $Mg^{2+}$) for lysing viral particles. Embodiments of the disclosure may employ chemical lysis methods including, for example, micelle-based methods. Methods may include using micelles to deliver suitable lysis agents. Suitable lysis agents include Tween 20, Tween 80, DDM Sarkosyl, SDS, and Triton X-100. One or more surfactants is used to micellize the lysis agent into the oil phase. Suitable surfactants for creating micelles may include, for example Ran or ionic Krytox. It may be useful to use a super-concentrated co-solvent to aid dissolution of the lysis agent. Some embodiments use a combination of fluoro-phase surfactant Krytox 157-FSH (acidic form) or neutralized form (ammonium counter-ion, potassium counter-ion or sodium counter-ion) in 0.05%-5% in Novec 7500 or 7300 or 7100 or Fuorinert to form micelles that include a lysis agent such as Sarkosyl or SDS at 0.05%-5%. In certain embodiments, a fluoro-phase surfactant such as Perfluorpolyether PEG-conjugates is used with a non-ionic lysis agent such as Triton-X100 or IGEPAL at 0.05%-2%. Fluorocarbon based oil system may be used, e.g., 3M Novec HFE (e.g. HFE7000, 7100, 7200, 7300, 7500, 7800, 8200) or 3M Fluorinert (e.g. FC-40,-43,-70,-72,-770-3283,-3284).

Embodiments may use surfactant for fluorocarbon based oil, e.g., commercially available compounds such as Chemour Krytox 157FSH, Chemour Capstone etc. Ionic type fluorophase surfactants may include Perfluoroalkyl carboxylates, Perfluoroalkyl sulfonates, Perfluoroalkyl sulfates, Perfluoroalkyl phosphates, Perfluoropolyether carboxylates, Perfluoropolyether sulfonates, or Perfluoropolyether phosphates. Non-ionic type fluorophase surfactant may include Perfluoropolyether ethoxylates or Perfluoroalkyl ethoxylates. A silicone based oil system may be used such as polydimethylsiloxane (PDMS) with viscosity range between 0.5-1000 cst. Suitable surfactant for silicone based oil may be used such as Gelest Reactive Silicones, Evonik ABIL surfactant, etc. An ionic type silicone phase surfactant may be carboxylate terminated PDMS or Amine terminated PDMS. A non-ionic type silicone phase surfactant may be hydroxyl terminated PDMS or PEG/PPG functionalized PDMS. A hydrocarbon based oil system may use heavy alkane hydrocarbons with carbon atoms number greater than 9. The oil could include a single compound or a mixture from multiple compounds. For example, tetradecane, hexadecane, mineral oil with viscosity range between 3 to 1000 cst. Suitable surfactant for hydrocarbon based oil (ionic) may include Alkyl carboxylates, Alkyl sulfates, Alkyl sulfonates, Alkyl phosphates or (non-ionic) PEG-PPG copolymers (e.g. Pluronic F68, Pluronic F127, Pluronic L121, Pluronic P123), PEG-alkyl ethers (e.g. Brij L4, Brij 58, Brij C10), PEG/PPG functionalized PDMS (e.g. Evonik ABIL EM90, EM180), Sorbitan derivatives (e.g. Span-60, Span-80, etc.), or Polysorbate derivatives (e.g. Tween-20, Tween 60, Tween 80). To achieve best micellization/co-dissolution performance and minimum disruption of water-in-oil droplet interface, the general rule of thumb for lysis agent/oil phase surfactant combination is as follow: (i) an ionic type lysis agent is preferred for combination with ionic oil phase surfactant, such lysis agent may include but not limited to: SDS, Sarkosyl, sodium deoxycholate, Capstone FS-61, CTAB; (ii) a non-ionic type lysis agent is preferred for combination with non-ionic oil phase surfactant, such lysis agent may include but not limited to: Triton X-100, Triton X-114, NP-40, Tween-80, Brij 35, Octyl glucoside, octyl thioglucoside; and/or (iii) a zwitterionic type lysis agent may be used in combination with either ionic or non-ionic oil phase surfactant, such lysis agent may include but not limited to: CHAPS, CHAPSO, ASB-14, ASB-16, SB-3-10, SB-3-12.

In some aspects, a sample may be obtained for the tissue or bodily fluid of a patient or from a swab taken from a patient. The sample may include a fine needle aspirate, a biopsy, or a bodily fluid from the patient. The sample may be processed, for example, to generate a suspension with an appropriate solution. Such solution will generally be a balanced salt solution, e.g. normal saline, PBS, Hank's balanced salt solution, etc., and in certain instances supplemented with fetal calf serum or other naturally occurring factors, in conjunction with an acceptable buffer at low concentration, generally from 5-25 mM. Convenient buffers include HEPES, phosphate buffers, lactate buffers, etc. In a preferred embodiment, the sample is a respiratory swab (e.g., a buccal, nasal, or throat swab). The swab may be placed into a sterile tube with a medium (e.g., Hank's balanced salt solution). The medium may also include antibiotics to reduce the possibility of bacterial contamination. The sample may be diluted prior to contacting the sample with the template particles. In some aspects, the viral nucleic acids are released and enriched prior to contact with the template particles. Several methods and commercially available products exist to isolate and enrich viral nucleic acids from a sample, for example, the QIAGEN® (Venlo, Netherlands) EZ1® DSP virus kits and Thermo Fisher Scientific® (Waltham, MA) MagMAX® viral pathogen kits.

In some aspects, the template particles have virus particle capture moieties tethered to them. Viral capture moieties may comprise any material that selectively binds to a virus particle. For example, a capture moiety may comprise an antibody. There are several methods for producing antibodies known in the art. Antibodies useful for the disclosure are commercially available, such as those produced by ProSci® (San Diego, CA).

In methods and systems of the disclosure, viral nucleic acids or their derived amplicons are sequenced, which may be performed by methods known in the art. For example, see, generally, Quail, et al., 2012, "A tale of three next generation sequencing platforms: comparison of Ion Torrent, Pacific Biosciences and Illumina MiSeq sequencers", BMC Genomics 13:341. Nucleic acid sequencing techniques include classic dideoxy sequencing reactions (Sanger method) using labeled terminators or primers and gel separation in slab or capillary, or preferably, next generation sequencing methods. For example, sequencing may be performed according to technologies described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

The conventional pipeline for processing sequencing data includes generating FASTQ-format files that contain reads sequenced from a next generation sequencing platform, and aligning these reads to an annotated reference genome. These steps are routinely performed using known computer algorithms, which a person skilled in the art will recognize can be used for executing steps of the present invention. For example, see Kukurba, Cold Spring Harb Protoc, 2015 (11): 951-969, incorporated by reference.

The sequence reads may be analyzed to identify mutations. For example, sequence reads derived from a fragment of amplified ctDNA may be analyzed to identify small mutations such as polymorphisms or small indels. To identify small mutations, reads may be mapped to a reference using assembly and alignment techniques known in the art or developed for use in the workflow. Various strategies for the alignment and assembly of sequence reads, including the assembly of sequence reads into contigs, are described in detail in U.S. Pat. No. 8,209,130, incorporated herein by reference. Strategies may include (i) assembling reads into contigs and aligning the contigs to a reference; (ii) aligning individual reads to the reference; or (iv) other strategies known to be developed or known in the art. Sequence assembly can be done by methods known in the art including reference-based assemblies, de novo assemblies, assembly by alignment, or combination methods. Sequence assembly is described in U.S. Pat. Nos. 8,165,821; 7,809,509; U.S. Pat. 6,223, 128; U.S. Pub. 2011/0257889; and U.S. Pub. 2009/0318310, the contents of each of which are hereby incorporated by reference in their entirety. Sequence assembly or mapping may employ assembly steps, alignment steps, or both. Assembly can be implemented, for example, by BLAST (basic local alignment search tool) (National Center for Biotechnology Information), DIAMOND, Kraken (see, Wood and Salzberg, Genome Biol, 15, R46 (2014), incorporated by reference), and MUSCLE (see, Edgar, Nuc Acid Res, 32 (5): 1792-7 (2004), incorporated by reference) and other bioinformatics programs known in the art.

The sequence reads obtained by methods and systems of the disclosure may be used for phylogenetic analysis. Bioinformatics tools such as BEAST (Bayesian evolutionary analysis by sampling trees) (see, Drummond and Rambaut, BMC Evolutionary Biology, 7:214 (2007), incorporated by reference) can be used for such analyses. These analyses can be used to identify novel viruses and substrains, such as the unique substrains of SARS-COV-2 identified by Teng et al., "On the origin and continuing evolution of SARS-COV-2", DOI: 10.1093/nsr/nwaa036 (2020), incorporated by reference. Phylogenetic tools such as Nexstrain (see, Hadfield et al., Bioinformatics, 34 (23) 4121-4123 (2018), incorporated by reference) may also be used to track the spread and mutation of a virus.

Exemplary methods and systems of the disclosure are diagnostic tests. Diagnostic tests may be used to determine whether a patient is infected with a particular disease, for example, SARS-COV-2. An exemplary diagnostic test includes obtaining a respiratory swab, such as a buccal or nasal swab, from a patient. The swab is processed, and the resulting sample is diluted in an aqueous solution. Template particles decorated with antibodies specific to SARS-COV-2 spike or envelope proteins are added to the diluted sample. Appropriate antibodies include SARS-COV-2 Spike antibody (No. 3525) and SARS-COV-2 Envelope antibody (No. 3531) commercially available from ProSci, (San Diego, CA). Template particles with captured SARS-CoV-2 virus particles are washed and put in an aqueous solution. An oil is added to the aqueous solution, and the mixture is vortexed to simultaneously form monodisperse emulsion droplets with a single template particle and single virus particle in each droplet. Virus particles segregated the monodisperse emulsion droplets are lysed at a high temperature with controlled $Mn^{2+}$ or $Mg^{2+}$ mediated fragmentation of the released viral genomic RNA. The fragmented viral genomic RNA is captured by capture probes attached to the template particles segregated inside the emulsion droplets. Each capture probe comprises a specific barcode sequence and a random hexamer capture sequence. The barcodes are unique to the specific template particle to which they are attached. Thus, all captured viral genomic RNA within a droplet is labelled with a common identifying sequence. The emulsion particles are lysed in the presence of a fragmentation quenching buffer, and cDNA is generated from the captured viral genomic RNA. Libraries are generated by amplifying the cDNA with sequencing-compatible primers, such as those commonly used in Illumina® (San Diego, CA) sequencing methodologies. The libraries are then sequenced. The resulting sequence reads are assembled and aligned using a bioinformatics software. The reads may be compared to reference viral genomes to determine the identity of a virus in a sample.

It has been reported that SARS-COV-2 has a greater alignment with a bat coronavirus than it does to SARS-COV. (see, Zhou et al., Nature online, Feb. 3, 2020, incorporated by reference). Further, antibodies have shown cross reactivity for SARS-COV-2, SARS-COV, and certain bat coronaviruses. (Zhou et al.). This leads to inaccurate results in PCR and antibody-based testing. However, by sequencing the isolated virus particle, methods of the disclosure prevent misdiagnosis and misidentification of a virus in a sample. Further, sample indexing can be used to allow batch processing of multiple patient samples.

In a variation of the diagnostic test, a plurality of template particles is used, in which a portion is decorated with SARS-COV-2 antibodies and a portion with seasonal influenza antibodies. Appropriate seasonal influenza antibodies are commercially available, such as those from ProSci, (San Diego, CA). Thus, even though the two viruses may present overlapping symptoms, an accurate diagnosis can be made. The diagnostic test can also determine, using a single sample and workflow, whether a patient has a superinfection, i.e., concurrent infections caused by more than one disease.

In a further variation of the diagnostic test, the test uses a plurality of template particles in which respective portions of the template particles are decorated with antibodies for SARS-COV-2, seasonal influenza, rhinovirus, orthopneumovirus, parainfluenza viruses, and human metapneumovirus. These are all respiratory, RNA-based viruses that may present infections with overlapping symptoms. As the viruses are all RNA-based viruses, the diagnostic test is simplified because a reverse transcription step is universal to all captured viral RNA in a single sample.

Another exemplary diagnostic test includes obtaining a respiratory swab, such as a buccal or nasal swab, from a patient. The swab is processed, and the resulting sample is diluted in a resuspension buffer. The sample is centrifuged and the supernatant collected to remove cells and large debris. Free DNA in the sample is digested, for example, by the addition of DNAse. Residual mammalian mRNA may be depleted using polyT decorated magnetic beads to separate the mRNA from the remaining supernatant. Virus particles in the sample are lysed to release viral genomic RNA. The viral RNA may be fragmented using the application of heat and $Mg^{2+}$ or $Mn^{2+}$. The enriched viral RNA is combined with template particles in an aqueous solution. The capture probes comprise a particle-specific barcode sequence and a random hexamer capture sequence. The probes may also comprise a UMI. An oil is added to the aqueous solution, and the mixture is vortexed to simultaneously form monodisperse emulsion droplets with a single template particle with captured viral RNA in each droplet. The viral RNA is reverse transcribed, and the emulsion droplets lysed. The resulting cDNA has amplification sequences added by template switching oligonucleotides. A library of cDNA amplicons is created via a single PCR amplification with Illumina compatible sequencing primers. The amplicons are sequenced. The sequence reads are clustered using the barcodes and aligned to reference sequences for SARS-CoV-2, seasonal influenza, rhinovirus, orthopneumovirus, parainfluenza viruses, and human metapneumovirus. Barcode clustering is also used to quantify the number of captured viral genomes. In a variant of the diagnostic test, sample indexing is used to allow batch processing of multiple patient samples.

Other variants and equivalents are within the scope of the disclosure. A feature that is preferably in common among embodiments of the disclosure is that some form of vortexing, shaking, shearing, agitating, or mixing is performed to encapsulate a plurality of particles simultaneously into droplets while some reverse transcription occurs at least partially during the vortexing, shaking, shearing, agitating, or mixing stage. In certain methods, template particles capture virus particles and the shaking/vortexing to form droplets simultaneously form droplets that contain a single template molecule with a single captured virus particle. In certain methods, template particles capture virus genomic nucleic acids and the shaking/vortexing to form droplets simultaneously form droplets that contain a single template molecule with captured virus genomic nucleic acids. In certain methods in which viruses with RNA genomes are detected, the methods, either wholly or at least in part, the shaking/vortexing to form droplets is contemporaneous with synthesizing a cDNA copy of a viral RNA resulting in the cDNA copy being contained within the droplet, once formed. Because methods of the disclosure are useful for making cDNAs from viral RNA that may serve well as samples for sequencing or quantification assays (e.g., digital PCR, for example), methods of the disclosure are useful for preparing samples where the input includes viral RNA.

What is claimed is:

1. A virus detection method, the method comprising:
obtaining a sample comprising virus particles;
capturing virus particles from the sample with template particles in a first fluid within a vessel, wherein the template particles comprise a first plurality of first capture probes and a second plurality of second capture probes, and wherein the template particles comprise antibodies that capture the virus particles;
adding a second fluid immiscible to the first fluid to the vessel;
vortexing the vessel to simultaneously generate a plurality of monodisperse emulsion droplets that encapsulate a single template particle and a single virus particle from the sample;
lysing the virus particles contained within the monodisperse emulsion droplets to release a plurality of distinct viral genomic RNA;
capturing the plurality of distinct viral genomic RNA using a first capture probe of the first plurality of first capture probes, wherein the first capture probe comprises a first primer binding site and a first capture sequence;
forming cDNA using the captured plurality of distinct viral genomic RNA;
capturing the cDNA using a second capture probe of the second plurality of second capture probes, wherein the second capture probe comprises a second primer binding site different from the first primer binding site, wherein the second capture probe comprises a second capture sequence different from the first capture sequence, wherein the second capture sequence binds cDNA, wherein the second capture sequences of at least two individual second capture probes are different, and wherein the first capture probe, the second capture probe, or both, comprises a barcode sequence that is unique to a template particle;
providing each cDNA within a droplet the barcode unique to the template particles; and
sequencing the plurality of distinct viral RNA based on the cDNA to detect the presence of one or more viruses in the sample.

2. The method of claim 1, wherein the first fluid is an aqueous solution and the second fluid comprises an oil.

3. The method of claim 2, wherein the template particles comprise a hydrogel that includes agarose, alginate, a polyethylene glycol (PEG), a polyacrylamide (PAA), acrylate, acrylamide/bisacylamide copolymer matrix, azide-modified PEG, poly-lysine, polyethyleneimine, or any combination thereof.

4. The method of claim 3, wherein the barcode unique to the droplet is provided to the droplet by the template particle encapsulated by the droplet.

5. The method of claim 1, wherein the first capture sequence is a random N-mer between 6 and 12 nucleotides in length.

6. The method of claim 1, wherein the second capture sequence is a random hexamer.

7. The method of claim 1, further comprising fragmenting the RNA prior to reverse transcribing the plurality of distinct viral genomic RNAs.

8. The method of claim 1, wherein the antibodies are specific to a particular virus and the plurality of monodisperse emulsion droplets encapsulate a single template particle with a single virus particle of the particular virus from the sample.

9. The method of claim 8, wherein the antibodies are specific to SARS-COV-2 and the plurality of monodisperse emulsion droplets encapsulate a single template particle with a single SARS-COV-2 virus particle from the sample.

10. The method of claim 1, wherein the template particles are a plurality of different template particles that each capture a virus particle of a different virus.

11. The method of claim 10, wherein the different template particles comprise different antibodies.

12. The method of claim 11, wherein the different antibodies are each specific to a different virus and the plurality of monodisperse emulsion droplets encapsulate a single template particle with a single virus particle of the virus specific to antibody of the encapsulated template particle.

13. The method of claim 12, wherein the different antibodies are specific to SARS-COV-2 or seasonal influenza and the plurality of monodisperse emulsion droplets encapsulate a single template particle with a single SARS-COV-2 virus particle or a single seasonal influenza virus particle from the sample.

14. The method of claim 11, wherein the different antibodies are specific to SARS-COV-2, seasonal influenza, rhinovirus, orthopneumovirus, parainfluenza viruses, or human metapneumovirus and the plurality of monodisperse emulsion droplets encapsulate a single template particle with a single SARS-COV-2, seasonal influenza, rhinovirus, orthopneumovirus, parainfluenza viruses, or human metapneumovirus virus particle from the sample.

15. A virus detection method, the method comprising:
obtaining a sample comprising virus particles;
lysing the virus particles to release a plurality of distinct viral genomic RNA;
combining the plurality of distinct viral genomic RNA with template particles in a first fluid in a vessel, wherein the template particles comprise a first plurality of first capture probes and a second plurality of second capture probes, and wherein the template particles comprise antibodies that capture the virus particles;
adding a second fluid immiscible to the first fluid to the vessel;
vortexing the vessel to simultaneously generate a plurality of monodisperse emulsion droplets that encapsulate a single template particle and viral genomic nucleic acid from the sample;
capturing the plurality of distinct viral genomic RNA using a first capture probe of the first plurality of first capture probes, wherein the first capture probe comprises a first primer binding site and a first capture sequence;
forming cDNA using the captured plurality of distinct viral genomic RNA;
capturing the cDNA using a second capture probe of the second plurality of second capture probes, wherein the second capture probe comprises a second primer binding site different from the first primer binding site, wherein the second capture probe comprises a second capture sequence different from the first capture sequence, wherein the second capture sequence binds cDNA, wherein the second capture sequences of at least two individual second capture probes are different, and wherein the first capture probe, the second capture probe, or both, comprises a barcode sequence that is unique to a template particle;
providing each viral cDNA within the droplet a barcode unique to the template particles; and
sequencing the viral RNA based on the cDNA encapsulated in the monodisperse emulsion droplets to detect the presence of one or more viruses in the sample.

16. The method of claim 15, wherein the first fluid is an aqueous solution and the second fluid comprises an oil.

17. The method of claim 16, wherein the template particles comprise a hydrogel that includes agarose, alginate, a polyethylene glycol (PEG), a polyacrylamide (PAA), acrylate, acrylamide/bisacylamide copolymer matrix, azide-modified PEG, poly-lysine, polyethyleneimine, or any combination thereof.

18. The method of claim 17, wherein the barcode unique to the droplet is provided to the droplet by the template particle encapsulated by the droplet.

19. The method of claim 15, wherein the first capture sequence is a random N-mer between 6 and 12 nucleotides in length.

20. The method of claim 15, wherein the second capture sequence is a random hexamer.

21. The method of claim 15, wherein the capture probes further comprise a unique molecular identifier (UMI).

22. The method of claim 15, comprising detecting RNA viruses, and the viral particles release a plurality of distinct viral genomic RNAs.

23. The method of claim 15, further comprising reverse transcribing the plurality of distinct viral genomic RNAs.

24. The method of claim 23, wherein during vortexing the capture probes capture viral genomic RNAs and reverse transcribe the viral genomic RNAs into cDNAs.

* * * * *